United States Patent
Thompson et al.

(10) Patent No.: US 7,368,570 B2
(45) Date of Patent: May 6, 2008

(54) ORGANOMETALLIC COMPLEXES AS SINGLET OXYGEN SENSITIZERS

(75) Inventors: Mark E. Thompson, Anaheim, CA (US); Peter I. Djurovich, Long Beach, CA (US); Drew Murphy, San Diego, CA (US); Matthias Selke, South Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 285 days.

(21) Appl. No.: 10/913,931

(22) Filed: Aug. 6, 2004

(65) Prior Publication Data

US 2005/0176624 A1    Aug. 11, 2005

Related U.S. Application Data

(60) Provisional application No. 60/493,144, filed on Aug. 7, 2003.

(51) Int. Cl.
*C07F 15/00* (2006.01)
*A61K 31/555* (2006.01)

(52) U.S. Cl. .......................... 546/2; 548/101; 514/184; 514/185; 210/605; 530/400

(58) Field of Classification Search ............ 546/2; 548/101; 514/184, 185; 210/605; 604/20; 530/400
See application file for complete search history.

(56) References Cited

U.S. PATENT DOCUMENTS 6,413,708 B1    7/2002   Slusarek et al. ............ 430/566
2002/0182441 A1*  12/2002  Lamansky et al. .......... 428/690

OTHER PUBLICATIONS

Tyson et al., J. Phys. Chem. A, vol. 105, No. 35, pp. 8154-8161 (2001).*

Chemical Abstracts No. 136:332666 (2002).*
Chemical Abstract No. 103:95440 (1985).*
Adachi, Chihaya et al., "Nearly 100% Internal Phosphorescence Efficiency in an Organic Light Emitting Device," J. Appl. Phys., vol. 90, No. 10, Nov. 15, 2001 pp. 5048-5051.
DeRosa, Maria C. et al., "Photosensitized Singlet Oxygen and its Applications," Coordination Chemistry Reviews 233-234 (2002), pp. 351-371.
Ikai, Masamichi et al., "Highly Efficient Phosphorescence from Organic Light-Emitting Devices with an Exciton-Block Layer," Appl. Phys. Lett., vol. 79, No. 2, Jul. 9, 2001, pp. 156-158.
Lamansky, Sergey et al., "Highly Phosphorescent Bis-Cyclometalated Iridium Complexes: Synthesis, Photophysical Characterization, and Use in Organic Light Emitting Diodes," J. Am. Chem., Soc., 2001, 123, pp. 4304-4312.
Lamansky, Sergey et al., "Molecularly Doped Polymer Light Emitting Diodes Utilizing Phosphorescent Pt(II) and Ir(III) Dopants," Organic Electronics 2 (2001) pp. 53-62.
Lamansky, Sergey et al., "Synthesis and Characterization of Phosphorescent Cyclometalated Iridium Complexes," Inorg. Chem., 2001, 40, pp. 1704-1711.

* cited by examiner

*Primary Examiner*—Porfirio Nazario-Gonzalez
(74) *Attorney, Agent, or Firm*—Hogan & Haratson LLP

(57) ABSTRACT

A series of organometallic complexes and the singlet oxygen sensitization properties of these complexes are provided. Complexes with acetylacetonate ligands give singlet oxygen quantum yields near unity, whether exciting the ligand-based state or the lowest energy excited state (MLCT+$^3$LC). The singlet oxygen quenching rates for these β-diketonate complexes are small, roughly three orders of magnitude slower than the corresponding phosphorescence quenching rate. Similar complexes were prepared with glycine or pyridine tethered to the Ir(III) center (i.e. $(bsn)_2Ir(gly)$ and $(bt)_2Ir(py)Cl$, where gly=glycine, and py=pyridine). The glycine and pyridine derivatives give high singlet oxygen yields.

37 Claims, 12 Drawing Sheets

BSN: R = Me
BSN*: R = t-Bu

PQ

BT

C6

C6Pt(acac)

BSN-G

BT-py

BO

BTP   PQIrIC

PQIrH   BTIrIC

BTIrH

1NP-p3

1NP btPt(dpm)

Ir(ppy)$_3$ btpPt(acac)

BT-p2

PQ-aet btpPt(dpm)

ppyPt(acac)

(ppy)₂Ir(acac)

MPI-p₃ ppyPt(dpm)

(btp)₂Ir(acac)

FIrPic

(bpy)PtMe₂

(Phen)PtMe₂

(CyPh₂)PtMe₂

(tbbpy)PtMe₂

(PhenPh₂)PtMe₂

ORGANOMETALLIC COMPLEXES AS SINGLET OXYGEN SENSITIZERS

CROSS-REFERENCE TO RELATED APPLICATIONS

The present invention claims priority to Provisional Application Ser. No. 60/493,144, filed on Aug. 7, 2003, entitled "Heavy Metal Complexes as Singlet Oxygen Sensitizers," which is incorporated herein by reference in its entirety.

Support from the N1H-NIGMS MBRS program (Award number GM 08101) and DARPA (Grant number MDA972-01-1-0032) is acknowledged.

FIELD OF THE INVENTION

The present invention relates to organometallic complexes, such as Ir(III) complexes and Pt(II) complexes, and the use thereof as singlet oxygen sensitizers.

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

The photophysics of octahedral $4d^6$ and $5d^6$ coordination complexes has been studied extensively. These coordination complexes, particularly those prepared with Ru and Os, have been used in a variety of photonic applications, including photocatalysis and photoelectrochemistry. More recently, researches have investigated the photophysics of isoelectronic $Rh^{3+}$ and $Ir^{3+}$ complexes, with both diimine and cyclometallated ligands, such as 2-phenylpyridinato-$C^2$,N (ppy). The cyclometallated ligands are formally monoanionic and can thus be used to prepare neutral tris-ligand complexes, which are isoelectronic with the cationic trisdiimine complexes of Ru and Os, e.g., fac-M(ppy)$_3$, fac-M(2 (α-thiophenyl)-pyridine)$_3$ (fac=facial). The $d^6$ Ir complexes show intense phosphorescence at room temperature, while the Rh complexes give measurable emission only at low temperatures.

Recently, the chemistry of cyclometallated Ir(III) complexes has received a great deal of attention. These complexes have proven to be very efficient emissive dopants in molecular and polymeric light emitting diodes (1). For example, efficient multilayer devices with Irppy doped into a hole transporting polymer layer have been reported (14). Heavy metal complexes, particularly those containing Pt and Ir, can serve as efficient phosphors in organic light emitting devices. In these devices, holes and electrons are injected into opposite surfaces of a planar multiplayer organic thin film. The holes and electrons migrate through the thin film to a material interface, where they recombine to form radiated excited states, or excitons. This electrically generated exciton can be either a singlet or a triplet. Both theoretical predictions and experimental measurements give a singlet/triplet ratio for these excitons of 1 to 3. Fluorescent materials typically used to fabricate organic light emitting diodes (OLEDs) do not give detectable triplet emission (i.e., phosphorescence), nor is there evidence for significant inter-system crossing between the triplet and singlet manifolds at room temperature. The singlet/triple ratio thus implies a limitation of 25% for the internal quantum efficiency for OLEDs based on fluorescence. Strong spin orbit coupling of the metal ion in these OLED phosphors leads to efficient emission from a predominantly triplet excited state, which emits with a long radiative lifetime relative to fluorescent materials (phosphor lifetime=microseconds, fluorescent lifetime=nanoseconds), leading to efficient utilization of both singlet and triplet excitons. The long lifetimes in these phosphors are very useful for efficiently utilizing the excited state energy.

Photodynamic therapy ("PDT") is a new modality for the treatment of malignancies, diseased tissue or cells, hyperproliferating tissues, pathogens or unwanted normal tissues. Photodynamic therapy (PDT) is the use of an agent such as a photosensitizer, given orally, intravenously, or topically, that can be activated or energized by light. The photoactivating light excites the photosensitizer which, in turn, interacts with oxygen causing the production of the cytotoxic singlet oxygen species. The role of the photosensitizer in the production of singlet oxygen, i.e., that of a molecule which absorbs the incident light energy and transfers it to ground state oxygen, thereby elevating it to its singlet excited state which is the reactive intermediate. The interaction of the cytotoxic oxygen species with tissues in which the photosensitizer is localized causes a modification of the tissue, resulting in a desired clinical effect. Thus, photodynamic therapy involves the application of a photosensitive (photochemotherapeutic) agent either systemically or locally to an affected area of the body, followed by exposure of the photosensitive agent to light of a suitable wavelength to activate the photosensitive agent, whereby the affected cells are killed or their proliferative potential is diminished. The tissue specificity of the resultant phototoxic damage is determined largely, although not entirely, by the relative concentrations of the photosensitizer in each tissue at the time of its exposure to the photoactivating light.

Following systemic administration, many photosensitizers accumulate to varying degrees within tissues depending on the pharmacokinetic and distribution profile of the photosensitizing compound and the cell types comprising the tissues. The chemical factors that enable certain photosensitizers to accumulate to a greater degree at a target site than other photosensitizers is not well understood. Indeed, the biological factors that result in the preferential uptake of some photosensitizers in certain tissue types compared to other tissue types are not well understood either. It is clear, however, that each photosensitizer has its own distribution and pharmacokinetic properties within different tissues and these properties determine the relative usefulness of the photosensitizer for the desired therapy. Currently, rigorous screening and biological evaluation in appropriate model systems is required to identify suitable photosensitizers that display the characteristics necessary to effect a therapy within the diseased or target tissues. One critical problem that has not been addressed however is the differential uptake of the photosensitizer by the target cells relative to the other, normal, cells. Indeed, it is known that uptake is generally a function of the molecular structure of the dye being absorbed and that this property varies with different cell types.

It would therefore be highly desirable to be provided with a series of new photosensitizers that can be easily attached to side groups of histidine, other amino acids, and other biomolecules for use as selective photooxidizing agents for biological materials.

Waste water treatment is usually divided into three stages: primary, the removal of settleable solids; secondary, the removal of readily biodegradable contaminates; and tertiary treatment. Tertiary treatment is, generally, the further treatment of waste water after prior treatment has reduced the chemical oxygen demand (COD) to less than about 60 mg/L and the biochemical oxygen demand (BOD) to less than about 20 mg/L. It may also include the removal of disease causing agents, plant nutrients, synthetic organic chemicals, inorganic chemicals, heat, sediments and radioactive substances. Tertiary treatment processes include lime (or other chemical) clarification, filtration, activated carbon adsorption, and ozone treatment. Ozone ($O_3$), which is the most well known tertiary treatment method, is extremely valuable from an environmental point of view. The process oxidizes organic materials in an aqueous environment producing compounds which do not upset the normal biological equilibrium. Unfortunately, this process is expensive, requiring the initial construction of the plant followed by continued use of electricity and oxygen for its operation. U.S. Pat. No. 4,104,204 describes a process for treating aqueous waste effluents containing organic materials which comprises adding to said aqueous effluents in the presence of oxygen, a water insoluble polymer-based photosensitizer and then photolyzing the resulting suspension with light having wavelengths between 320 nm and about 800 nm.

SUMMARY OF THE INVENTION

The present invention provides novel organometallic complexes and methods of use thereof as singlet oxygen photosensitizers. More specifically, one aspect of the present invention provides highly emissive photosensitizers having the formula $(C^\wedge X)_n MY_m L_p$, where M is a metal; $C^\wedge X$ represents a bidentate cyclometallated ligand; L is a neutral ligand; Y is a monoanionic ligand; and n+m is 3 when M is trivalent or n+m is 2 when M is divalent. In both cases, the value of "p" is chosen to saturate the coordination shell of metal ion (six coordinate for octahedral and four coordinate for square planar or tetrahedral). In a preferred embodiment, X is N, O, S, P or C. In another preferred embodiment, M is Ir(III) or Pt(II).

Another aspect of this invention provides highly emissive organometallic photosensitizers having the formula $(C^\wedge X)_n M(L^\wedge Y)_m$, where M is a metal; $C^\wedge X$ represents a bidentate cyclometallated ligand wherein each $C^\wedge X$ is the same or different; $L^\wedge Y$ represents a bidentate cyclometallated ligand wherein each $L^\wedge Y$ can be the same or different; and n+m is 3 when M is trivalent or n+m is 2 when M is divalent. In one embodiment, X, Y and L are independently N, O, S, P or C. In another embodiment, M is Pt(II) or Ir(III).

Yet another aspect of this invention provides highly emissive organometallic photosensitizers having the formula $(C^\wedge X)_n M(C^\wedge X')_m$, wherein M is a metal; n+m is 3 when M is trivalent or n+m is 2 when M is divalent; and $C^\wedge X$ and $C^\wedge X'$ represent first and second bidentate cyclometallated ligands, respectively, wherein each $C^\wedge X$ and $C^\wedge X'$ is the same or different. In one embodiment, X and X' are independently N, O, S, P or C. In another embodiment, M is Pt(II) or Ir(III).

Yet another aspect of this invention provides highly emissive organometallic photosensitizers having the formula $(C^\wedge X)_3 Ir$, where $C^\wedge X$ represents a bidentate cyclometallated ligand and each $C^\wedge X$ is the same or different. In one embodiment, X is N, O, S, P or C.

According to another aspect, this invention provides methods of using the photosensitizers of this invention in photodynamic therapy (PDT). More specifically, this invention provides a method for causing photodynamic damage to target cells or biological tissue, said method comprising contacting the target cells or biological tissue with a photosensitizer of this invention so as to produce a population of treated cells; and exposing the population of treated cells to light at a wavelength that activates the photosensitizer, thereby producing singlet oxygen and causing photodynamic damage to the target cells or biological. In one embodiment, at least one of the $C^\wedge X$, $C^\wedge X'$, L, Y or $L^\wedge Y$ ligands is further coupled to a moiety that can bind to a biomolecule, cell or biological tissue.

The photosensitizers of the present invention may further be used for studying biological materials. A binding or coordination occurs between the photosensitizer and the biological material, such as a protein, in a sample or in vivo. The sample is then exposed to an energy source to bring the photosensitizer to its excited state where it will produce singlet oxygen. The amount of singlet oxygen produced is measured and the data is used to analyze the biological material.

The products of the invention method also include pharmaceutical compositions comprising the complexes of this invention.

The present invention further includes methods of using the photosensitizers of this invention to generate singlet oxygen for use in organic synthesis. In one embodiment, the method comprises subjecting an organometallic singlet oxygen sensitizer of this invention to light in the presence of oxygen.

This invention further relates to the treatment of waste water with an oxidation process thereby rendering the waste water more suitable for disposal or subsequent treatment. In particular, the present invention includes methods of using the photosensitizers of this invention for treating aqueous waste effluents containing organic materials, which comprises adding to said aqueous effluents in the presence of oxygen, a water insoluble photosensitizer of this invention and then photolyzing the resulting suspension with light having wavelengths between 400 nm and about 600 nm. In one embodiment, the photosensitizer is covalently attached to an inert support.

The sensitizers of the present invention do not react appreciably with the singlet oxygen and therefore are not consumed by the singlet oxygen they produce. Thus, the sensitizers of the present invention will have better lifetimes than known sensitizers.

The foregoing and other features, utilities and advantages of the invention will be apparent from the following more particular descriptions of preferred embodiments of the invention and as illustrated in the accompanying drawings and as particularly pointed out in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

DETAILED DESCRIPTION OF THE INVENTION

Figure 1A:
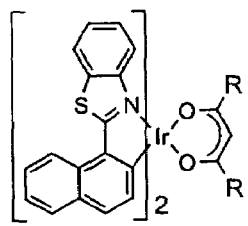
FIGS. 1A-1E show the structures of Ir(III) and Pt(II) sensitizers of the present invention.
Figure 1A:
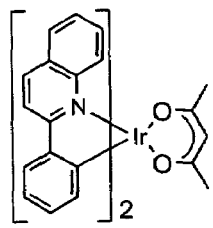
Figure 1A:
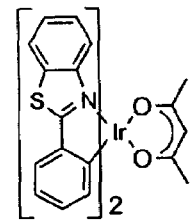
Figure 1A:
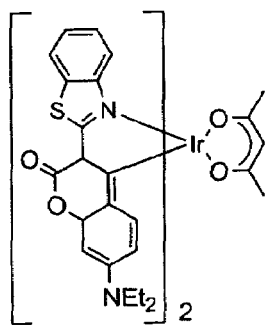
Figure 1A:
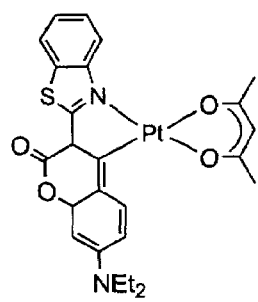
Figure 1A:
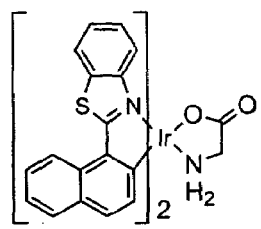
Figure 1A:
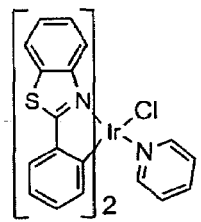
Figure 1A:
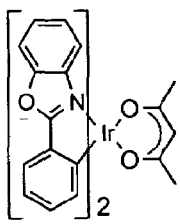
Figure 1B:
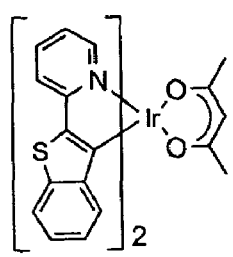
Figure 1B:
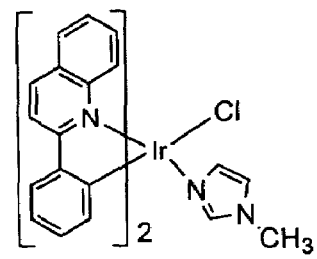
Figure 1B:
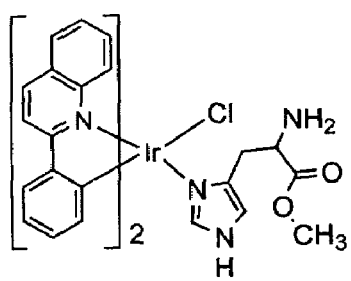
Figure 1B:
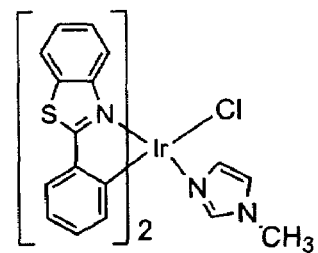
Figure 1B:
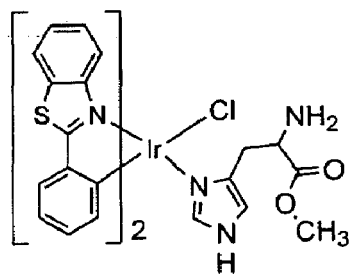
Figure 1C:
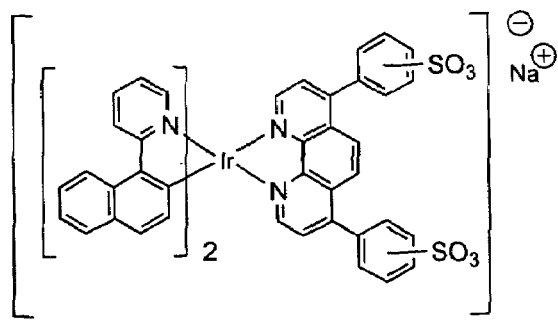
Figure 1C:
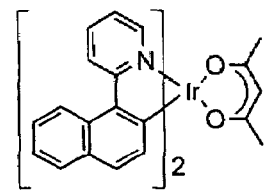
Figure 1C:
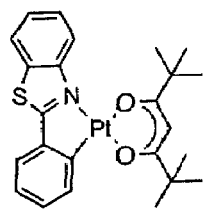
Figure 1C:
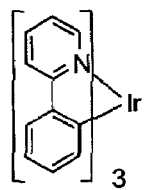
Figure 1C:
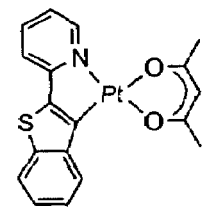
Figure 1C:
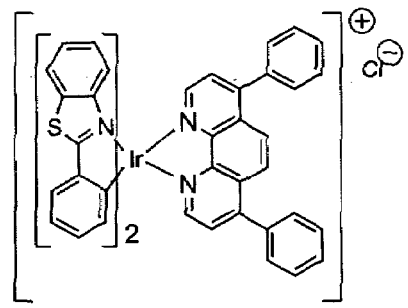
Figure 1C:
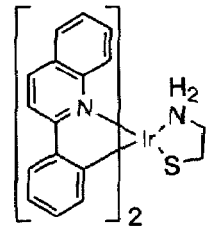
Figure 1D:
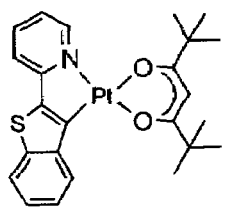
Figure 1D:
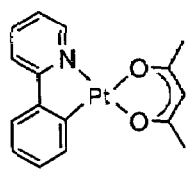
Figure 1D:
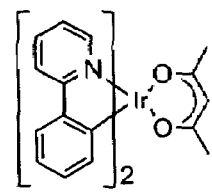
Figure 1D:
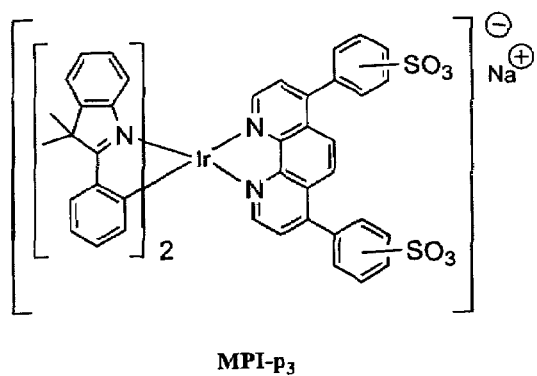
Figure 1D:
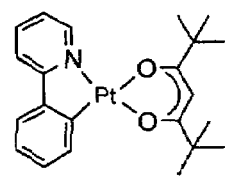
Figure 1D:
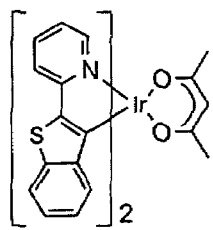
Figure 1D:
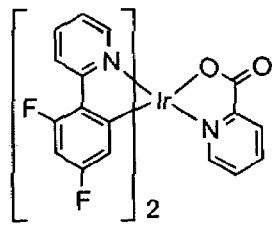
Figure 1D:
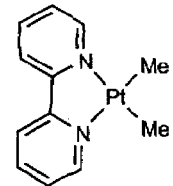
Figure 1E:
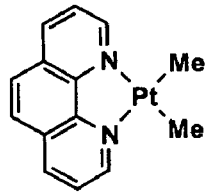
Figure 1E:
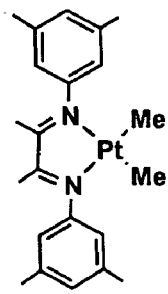
Figure 1E:
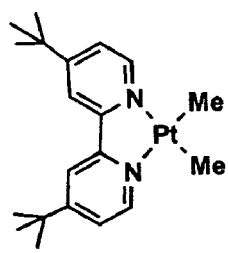
Figure 1E:
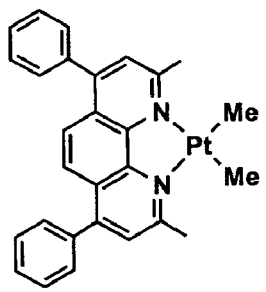

The present invention provides novel organometallic complexes and methods of use thereof as singlet oxygen photosensitizers. More specifically, the present invention provides organometallic singlet oxygen photosensitizers, comprising a metal ion and at least one ligand having a covalent metal-carbon bond between said metal ion and said ligand. In a preferred embodiment, at least one of the ligands is a bidentate cyclometallated ligand in which at least one of the binding sites is a carbon. The organometallic complexes of this invention preferably have quantum yields of at least 50% for singlet oxygen production.

An "organometallic" is a compound having bonds between one or more metal atoms and one or more carbon atoms of an organic group. In addition to metals and semimetals, elements such as boron, silicon, arsenic and selenium are considered to form organometallic compounds. The inventors discovered that the metal-carbon bonding in the organometallic complexes of this invention leads to significant metal-to-ligand charge transfers and long excited state lifetimes, both of which are important in efficiently converting ground state oxygen (i.e., triplet oxygen) into the singlet state.

As used herein, the terms "photosensitizer" and "sensitizer" are used interchangeably and refer to a moiety which, when stimulated by excitation with radiation of one or more wavelengths or other chemical or physical stimulus (e.g., electron transfer, electrolysis, electroluminescence or energy transfer), will achieve an excited state which upon interaction with molecular oxygen will produce singlet molecular oxygen. Interaction with the excited photosensitizer will, with the addition of other reagents, produce a detectable signal.

In one embodiment, the sensitizers of this invention the formula $(C^\wedge X)_n MY_m L_p$, where M is a metal; $C^\wedge X$ represents a bidentate cyclometallated ligand (i.e., a ligand having two binding sites C and X, wherein C and X are covalently linked through one or more atoms and wherein at least one of the binding sites is covalently bonded to M) wherein each $C^\wedge X$ is the same or different; L is a neutral ligand; Y is a monoanionic ligand; and n+m is 3 when M is trivalent or n+m is 2 when M is divalent. In both cases, the value of "p" is chosen to saturate the coordination shell of metal ion (six coordinate for octahedral and four coordinate for square planar or tetrahedral). In a preferred embodiment, X is N, O, S, P or C. The ligand $C^\wedge X$ can also be represented herein by the formula

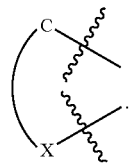

In one embodiment, M is a metal having an atomic weight of 40 or higher. In another embodiment, M is a metal selected from Ti, Zr, Hf, V, Nb, Ta, Cr, Mo, W, Mn, Tc, Re, Fe, Ru, Os, Co, Rh, Ir, Ni, Pd, Pt, Ti, Pb, Bi, In, Sn, Sb, Te, Au, and Ag. In a more preferred embodiment, M is Ir(III) or Pt(II).

In a preferred embodiment, a singlet oxygen photosensitizer of this invention comprises the formula $(C^\wedge X)_n MY_m L_p$, which can also be represented by the structure

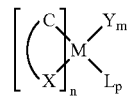

where M is Ir(III) or Pt(II);
$C^\wedge X$ is a bidentate cyclometallated ligand;
X is N, O, S, P or C;
n+m is 3 when M is Ir(III) or n+m is 2 when M is Pt(II);
Y is Cl;

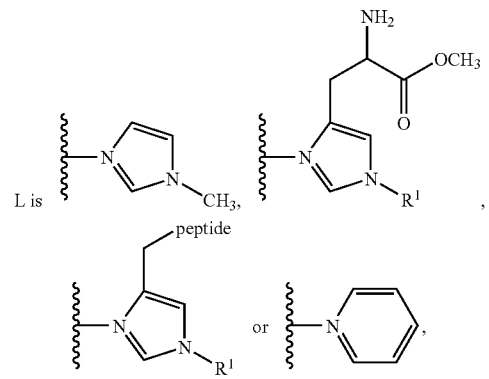

where $R^1$ is H or alkyl, or optionally when M is Ir(III) then Y and L are absent, and wherein each $C^\wedge X$ can be the same or different.

Example of suitable C^X ligands for any of the complex of this invention include, but are not limited to,

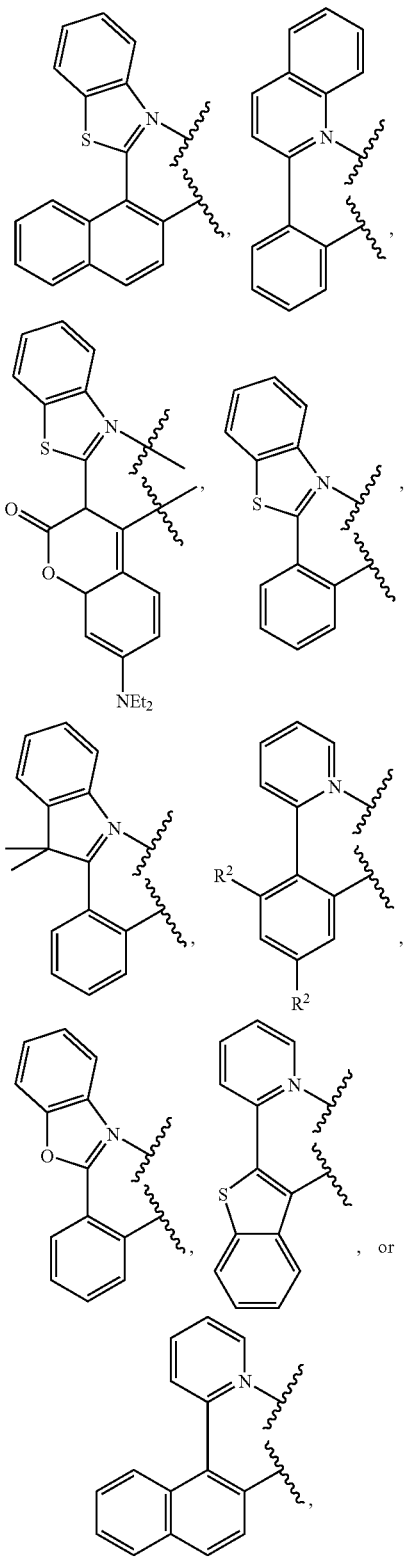

where R² is H or F.

According to another embodiment, the photosensitizers of this invention have the formula $(C^\wedge X)_n M(L^\wedge Y)_m$, which can also be represented by the structure

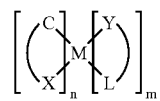

where M is a metal ion; C^X represents a first bidentate cyclometallated ligand wherein each C^X can be the same or different; L^Y represents a second bidentate cyclometallated ligand (i.e., a cyclic ligand having two binding sites L and Y, wherein L and Y are covalently linked through one or more atoms and wherein at least one of the binding sites is covalently bonded to the metal atom M) wherein each L^Y can be the same or different; n+m is 3 when M is trivalent or n+m is 2 when M is divalent. In both cases, the value of "p" is chosen to saturate the coordination shell of metal ion (six coordinate for octahedral and four coordinate for square planar or tetrahedral). In one embodiment, X, Y and L are independently N, O, S, P or C. In a preferred embodiment, M is Ir(III) or Pt(II). The ligand L^Y can also represented herein by the formula

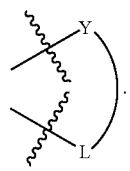

Examples of suitable L^Y ligands include, but are not limited to,

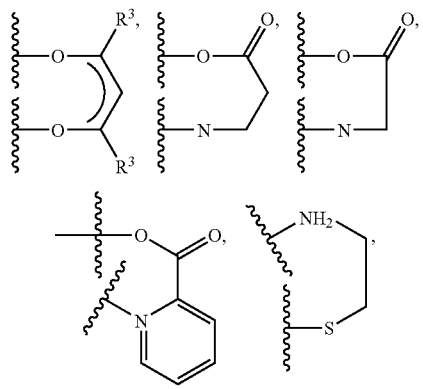

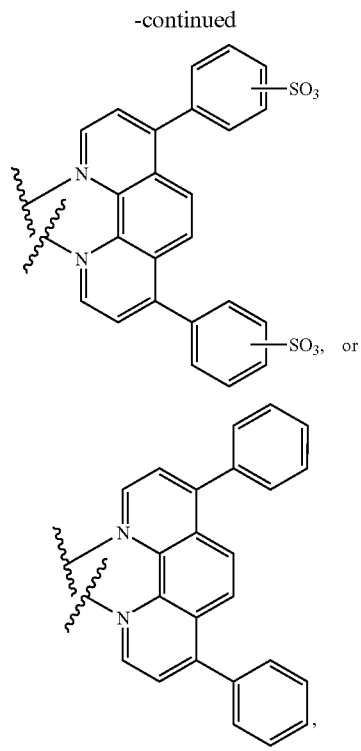

where R³ is CH₃ or t-butyl.

According to yet another embodiment, the photosensitizers of this invention have the formula $(C^{\wedge}X)_nM(C^{\wedge}X')_m$, which can also be represented by the structure $$\left[\begin{pmatrix} C \\ X \end{pmatrix}_n M \begin{pmatrix} C \\ X' \end{pmatrix}_m\right]$$

wherein M is a metal, n+m is 3 when M is trivalent and n+m is 2 when M is divalent, and $C^{\wedge}X$ and $C^{\wedge}X'$ represent first and second bidentate cyclometallated ligands, respectively, wherein each $C^{\wedge}X$ and $C^{\wedge}X'$ can be the same or different. In one embodiment, X and X' are independently N, O, S, P or C. In a preferred embodiment, M is Pt(II) or Ir(III). Suitable $C^{\wedge}X$ and $C^{\wedge}X'$ ligands can independently be selected from ligands including, but not limited to,

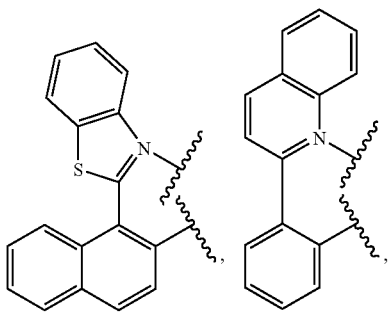

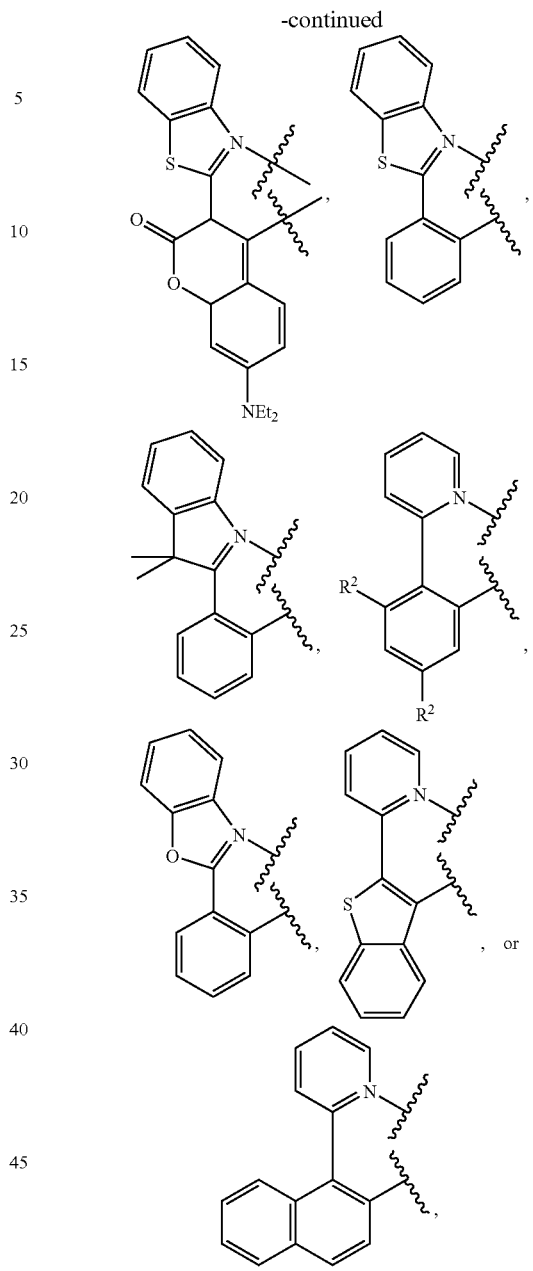

and R² is H or F.

According to yet another embodiment, the photosensitizers of this invention have the formula $(C^{\wedge}X)_3Ir$, where $C^{\wedge}X$ represents a bidentate cyclometallated ligand and each $C^{\wedge}X$ can be the same or different. In one embodiment, X is N, O, S, P or C.

Representative photosensitizers of this invention having various $C^{\wedge}X$, L, Y and $L^{\wedge}Y$ ligands are shown in FIGS. 1A-1E. In FIGS. 1A-1E, the abbreviations used for the ligands of the inventive complexes are as follows: bt=2-phenylbenzothiazole; bsn=2-(1-naphthyl)benzothiazole; pq=2-phenylquinoline; acac=acetylacetonate; gly=glycine, and py=pyridine. According to one method, a synthetic procedure used to prepare these complexes involves two steps. In the first step, IrCl₃·nH₂O is reacted with an excess of the desired $C^{\wedge}X$ ligand to give a chloride-bridged dimer, i.e., C^N$_2$Ir(μ–Cl)$_2$C^N$_2$ (Equation 1). The chloride-bridged dimer can be readily converted to an emissive, monomeric complex of this invention by replacing the bridging chlorides with bidentate, monoanionic β-diketonate ligands (L^Y) as shown in Equation 2. These reactions give (C^N)$_2$IrL^X with a yield of typically >80%.

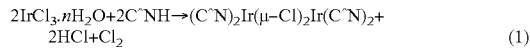  (1)

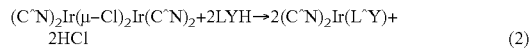  (2)

While studying the photophysical properties of the complexes shown in FIGS. 1A-1E, it was observed that the quantum efficiencies and triplet lifetimes are severely reduced by oxygen (1a, 2), only giving high values (φ>0.5 and τ>2 μsec) for rigorously degassed samples. The observed reduction in quantum efficiencies and triplet lifetimes by oxygen prompted the inventors to investigate these complexes as potential singlet oxygen sensitizers, since singlet oxygen formation is a possible quenching process. The inventors discovered that a variety of cyclometallated Ir(III) and Pt(II) complexes are useful photosensitizers for the production of singlet oxygen with generally high quantum efficiencies and small concomitant physical quenching of singlet oxygen.

The lowest energy (emissive) excited state of these complexes is a mixture of MLCT and $^3$(π-π*) states (1a), composed principally of C^N ligand orbitals, with the β-diketonate ligand (FIG. 1; complexes BSN, BSN*, PQ and BT) acting as an ancillary ligand. Stern-Volmer analysis shows that phosphorescence from these complexes is efficiently quenched by triplet oxygen, at near diffusion controlled rates. Table 1 provides the quantum yields for singlet oxygen generation, ($\Phi_A$), phosphorescence quenching rates ($k_{q,SV}$) and singlet oxygen quenching rates ($k_q(^1O_2)$) for BSN, BSN*, PQ, BT, BSN-G and BT-py.

TABLE 1

| Sensitizer[a] | λ (nm) | $\Phi_A$[b] | $k_{q,SV}$ (10$^9$ M$^{-1}$s$^{-1}$) | $k_q(^1O_2)$ (10$^6$ M$^{-1}$s$^{-1}$) |
|---|---|---|---|---|
| BSN | 355 | 0.59 ± 0.07 | | 6.3 ± 0.2 |
| | 532 | 0.89 ± 0.02 | | |
| BSN* | 355 | 0.60 ± 0.06 | 2.9 ± 0.1 | 4.0 ± 0.3 |
| | 532 | 0.77 ± 0.08 | | |
| PQ | 355 | 0.62 ± 0.05 | 7.2 ± 0.3 | 1.0 ± 0.2 |
| | 532 | 0.89 ± 0.07 | | |
| BT | 355 | 0.86 ± 0.07 | | 0.5 ± 0.2 |
| | 532 | 1.00 ± 0.07 | 5.9 ± 0.6 | |
| BSN-G | 355 | 0.54 ± 0.02 | | 2.1 = 0.5 |
| | 532 | 0.81 ± 0.06 | | |
| BT-py | 355 | 0.95 ± 0.09 | | None detected |
| | 532 | 1.00 ± 0.09 | | |

[a]: Measurements were made in benzene. [b]: References for quantum yield measurements were C$_{60}$ (0.76), TPP (0.62) and Perinaphthenone (0.95) at 355 nm and TPP (0.62) at 532 nm.

The efficient oxygen quenching involves the formation of singlet oxygen, as all of the Ir(III) complexes shown in Table 1 proved to be excellent singlet oxygen sensitizers. The quantum yields for singlet oxygen production ($\Phi_A$) were obtained by measuring the intensity of the $^1O_2$ luminescence signal ($\lambda_{max}$=1268 nm). Measurements were taken with 355 and 532 nm excitation (λ), in air-saturated solutions. Triplet-triplet annihilation was negligible at these concentrations, as evidenced by the fact that the $^1O_2$ intensity did not decrease at higher concentrations, as it would if T-T annihilation were depleting the excited photosensitizer.

Figure 2:
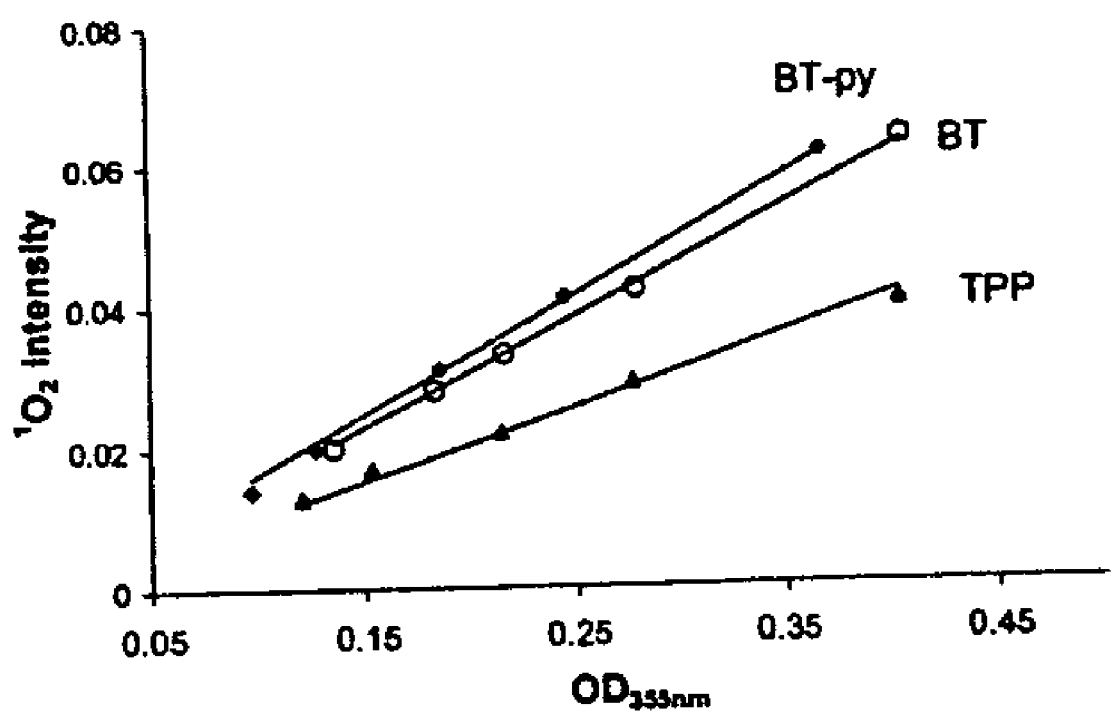
FIG. 2 is a graph of the relative intensity of singlet oxygen production vs. absorbance for the Ir(III) complexes BT, BT-py and for the reference compound TPP at 355 nm ($OD_{355\,nm}$).

FIG. 2 shows the relative intensity of singlet oxygen production vs. absorbance for the iridium complexes BT, BT-py and for TPP at 355 nm (OD$_{355\ nm}$). The singlet oxygen quantum yields are very large and near unity for all of the β-diketonate complexes examined. The $\Phi_A$ values are high for both ligand based excitation (355 nm) and direct excitation of the lowest energy excited state (MLCT+$^3$LC) with 532 nm light.

Iridium complexes are known to form singlet oxygen upon optical excitation (e.g. [Ir(bpy)$_3$]$^{3+}$ and [Ir(phen)$_3$]$^{3+}$ (4)). However, many iridium complexes also quench singlet oxygen efficiently (5). Large $^1O_2$ quenching rates would severely limit potential applications of the bis-cyclometallated iridium complexes as photosensitizers. The inventors therefore determined singlet oxygen quenching rates [$k_q$ ($^1O_2$)] for all of the iridium complexes of the present invention (Table 1). The quenching rates for all of the complexes having a β-diketonate ancillary ligand (BSN, BSN*, PQ and BT) were found to be small, ranging from (10±2)×10$^5$ M$^{-1}$sec$^{-1}$ for PQ to (6±0.2)×10$^6$ M$^{-1}$sec$^{-1}$ for BSN. These singlet oxygen quenching rates are roughly three orders of magnitude slower than the phosphorescence quenching rates ($k_{qSV}$), consistent with the high $\Phi_A$ values observed here. For the BT complex the singlet oxygen quenching rate is in fact smaller than those of many standard singlet oxygen sensitizers such as tetraphenylporphyrin (TPP) [$k_q$=(6±2)×10$^7$ M$^{-1}$s$^{-1}$] (6), while the quantum yield is near unity. Even though the cyclometalling ligands of BSN, BSN*, PQ and BT give rise to very different absorption and emission energies (1a, 3), the efficiencies of the complexes for singlet oxygen production are very similar. Based on spectroscopic measurements for these four complexes (1a), the orbital make-up for the triplet excited states are similar, and largely ligand based (i.e. π-π*). While not wanting to be bound by any particular theory, the inventors believe that this similarity may be the reason why they have similar efficiencies for $^1O_2$ generation. The slight decrease of $\Phi_A$ of BSN at 532 nm relative to BSN* at 532 nm appears to be out of the error range and may be due to a steric blocking effect.

Many of the sensitizers of the present invention that have β-diketonate L^X ligands are resistant toward irradiation under aerobic conditions, since no significant decomposition was detected for irradiation times of up to 60 minutes.

The inventors have also demonstrated that complexes with three cyclometallating ligands will act as efficient singlet oxygen photosensitizers, i.e., complexes having the formula (C^X)$_3$Ir, such as Ir(ppy)$_3$. Thus, it appears that an important component in achieving good singlet oxygen formation and low rates of singlet oxygen quenching is the presence of strongly bound, cyclometallated ligands and a full coordination shell around the central metal atom.

It is believed that that complexes of this invention with mixed cyclometallated ligands, i.e., (C^X)$_n$M(C^X'), will also be effective singlet oxygen photosensitizers. In these mixed ligand complexes one can design one ligand to efficiently absorb light at the desired wavelength (for example, for maximum depth penetration in tissue) and the other ligand to simultaneously bind to the metal center and to biological tissue or other materials. An example of such a ligand is an o-pheylpyridine ligand for binding to the metal and a specific ligand for a particular cellular receptor bound to either the phenyl of pyridyl group. The ligand-receptor pair could be chosen to specifically target binding of the metal-based PTD agent to a particular cell type or diseased tissue. The same approach could also be applied to a (C^X)$_n$M(L^Y) or (C^X)$_n$M(L)Y complex, at least one of the C^X, L^Y, L or Y ligands is further coupled to a tissue or cellular targeting moiety that allow the sensitizer to bind to the target biomolecule or biological tissue in PDT therapy, e.g., without a direct metal-protein or metal-nucleotide binding. Examples of such moieties that can bind to biomolecules or biological tissues include, but are not limited to, antibodies, oligonucleotides, DNA binding proteins and cell adhesion molecules. In one embodiment, the ligand is coupled to the moiety through covalent bonds.

While all of the organometallic Ir complexes of the present invention are efficient sensitizers for singlet oxygen, the Pt complexes were not uniformly effective. The cyclometallated derivatives disclosed herein produced singlet oxygen, while the specific dialkyl derivatives shown in Table 3 did not. The dialkyl derivatives do not show any detectable emission at room temperature and are very efficient quenchers of singlet oxygen. In contrast, the cyclometallated derivatives emit strongly at room temperature and have comparatively low singlet oxygen quenching rates. Two possible explanations for the failure of the specific dialkyl Pt derivatives shown in Table 3 to sensitize singlet oxygen are that the excited state lifetime is too short to interact with triplet oxygen before decay or that the formed singlet oxygen is immediately quenched by the Pt complex.

One of the more promising new modalities currently being explored for use in the control and treatment of tumors is photodynamic therapy (PDT). This technique is based on the use of a photosensitizing dye, which localizes at, or near, the tumor site, and when irradiated in the presence of oxygen serves to produce cytotoxic materials, such as singlet oxygen, from otherwise benign precursors. The putative action mechanism in PDT is that singlet oxygen generated by energy transfer from the triplet state of the photosensitizer to tumor oxygen initiates lipid peroxidation in the endothelial cells of the small blood vessels supplying the tumor cells. This process shuts down the tumor oxygen supply and induces the observed necrosis. Direct cancer cell killing may be involved as well. The drug properties deemed favorable for PDT include synthetic purity, effectiveness at far-red and near infrared wavelengths where tissues are more transparent, and short-term photosensitization of the patient's skin. In marked contrast to current methods (e.g., conventional chemotherapy), in PDT the drugs themselves can be completely innocuous until "activated" with light by an attending physician. Thus a level of control and selectivity may be attained which is not otherwise possible.

Accordingly, another aspect of this invention provides a method of using the photosensitizers of this invention in photodynamic therapy (PDT). The invention utilizes PDT methods that generally include the administration of a photosensitizer of this invention to a patient followed by irradiation with a wavelength of electromagnetic radiation capable of activating the photosensitizer. Activation of the photosensitizer generates singlet oxygen, which in turn causes damage to the target cells (e.g., tumor cells). Administration of the photosensitizer can be local or systemic. Examples of diseased tissues and cells that can be treated according to the method of this invention include, but are not limited to, cancerous cells such as common precancerous skin lesions, and intimal hyperplasia.

The invention also includes use of a photosensitizer in the preparation of a medicament for use in any of the methods described herein. Administration of the photosensitizer may be by delivery using any appropriate means including, but not limited to, systemic, local, or even direct application to the target tissue. Local delivery of the photosensitizer provides a high local concentration while reducing the likelihood of transient skin photosensitivity or other undesirable side effects that may follow systemic administration of the photosensitizer.

Singlet oxygen also reacts with many organic compounds including olefins, dienes, sulphides, aromatics, hetero-aromatics, terpenes, steroids, fatty acids, flavones, tetracyclines, vitamins, amino acids, proteins, nucleic acids, blood and bile pigments, and synthetic polymers Most of the reactions fall into three general classes: (1) The Aene reaction, which is a general type of reaction which is essentially a hydrogen abstraction and oxygen addition; (2) cycloaddition with a carbon-carbon double bond; and (3) oxygenation. Accordingly, the photosensitizers of this invention can be utilized for the production of singlet oxygen in various synthetic reactions. In one embodiment, the method of this invention comprises subjecting an organometallic photosensitizer of this invention to light in the presence of oxygen. For example, a light source having a wavelengths between 400 nm and about 800 nm can be used to activate the photosensitizer. Any suitable light source can be used to achieve the desired effect.

Singlet oxygen is capable of damaging nucleic acids, proteins, and lipids in the cellular environment. The reactions of singlet oxygen with nucleotide bases and amino acids have been the subject of intensive research for several decades (7). However, there have been few studies on the variation of $\phi_\Delta$ upon attachment of the photosensitizer to an amino acid residue. While the β-diketonate ligands of complexes BSN, PQ and BT are useful ancillary ligands, they are not appropriate models for biologically relevant ligands. Therefore, in order to investigate the potential of cyclometallated Ir(III) complexes as singlet oxygen sensitizers when coordinated to biomolecules, Ir(III) complexes having glycine and pyridine/chloride ligands were prepared (FIG. 1, complexes BSN-G and BT-py, respectively). The reaction between a Cl bridged iridium dimer and a given Lewis base is a straightforward process (8). The Cl bridged dimer is readily cleaved by Lewis base, such as pyridine or glycine, to give the desired iridium complex, as shown in Equation (3). Equation (4) shows the synthesis of derivatives BSN-G and BT-py by this method. The glycine derivatives form a chelated structure (BSN-G), while the pyridyl derivatives retain a terminal Cl ligand (BT-py). The pyridyl group (py) is a good model for the imidazole side group of histidine, while the coordinated glycine group (G) is a good model for amine side groups, such as those of lysine, as well as carboxylic acid side groups such as those of aspartic and other carboxyl-containing amino acids.

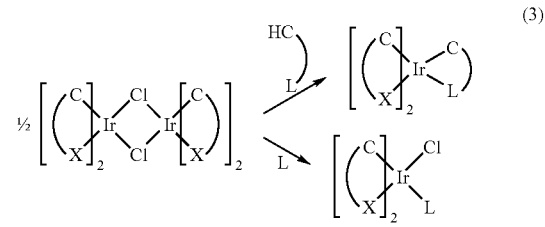

(3)

-continued (4)

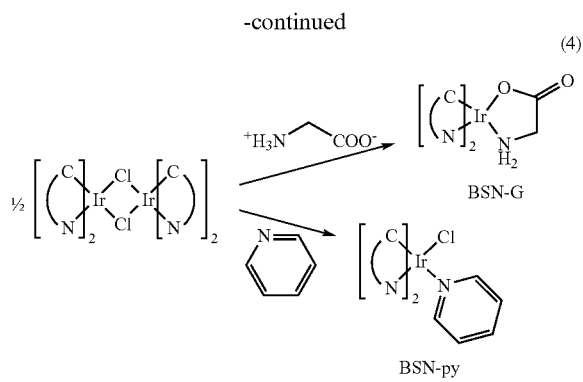

The singlet oxygen quantum yields for the glycine derivative BSN-G were similar to that of the related P-diketonate complexes, consistent with the "$(C^{\wedge}X)_2Ir$" fragment being responsible for the observed photophysics. The pyridyl derivative (BT-py) also showed a high quantum yield for singlet oxygen production and no measurable singlet oxygen quenching. Neither the presence of a terminal chloride nor the non-chelating nature of the single Lewis base ligand prevented the efficient formation of singlet oxygen by these complexes.

The high quantum yields for the glycine and pyridyl complexes and the remarkable ease by which amino acids can be attached to the sensitizers demonstrate that these sensitizers could indeed be used to study oxidative damage to the peptide chain via photogenerated singlet oxygen. The fact that a wide range of different Ir(III) dimer complexes are accessible and can be easily attached to side groups of histidine, other amino acids, and other biomolecules makes the complexes of the present invention particularly good candidates for use as photosensitizers for the generation of singlet oxygen and thus potentially useful for the inactivation or destruction of tumors. For example, in one embodiment, photodynamic tumor therapy comprises administering an Ir(III) or Pt(II) complex of this invention to a tumor host and irradiating the complex in proximity to the tumor.

This invention further relates to the treatment of waste water with an oxidation process thereby rendering the waste water more suitable for disposal or subsequent treatment. In particular, the present invention includes methods of using the photosensitizers of this invention for treating aqueous waste effluents containing organic materials, which comprises adding to said aqueous effluents in the presence of oxygen, a water insoluble photosensitizer of this invention and then photolyzing the resulting suspension with light having wavelengths between 400 nm and about 800 nm. In one embodiment, the method is achieved by covalently bonding the sensitizer to an inert polymer support. Since the sensitizers of the present invention do not react appreciably with the singlet oxygen, they are not consumed by the singlet oxygen they produce. Thus, the supported metal complexes of this invention used in water treatment processes will have better lifetime than those methods that use dyes as photosensitizers. Further, the method of this invention utilizes sensitizers that are covalently attached to the polymer support, which will prevent the eventual loss of the sensitizer into the water stream. In addition, with the increased singlet oxygen sensitization efficiencies of the sensitizers of this invention, increased efficiencies and thus lower material demands to achieve the same level of purity will be achieved.

EXAMPLES

Three of the complexes of the present invention (BSN, PQ, and BT) were prepared as reported previously (8). The characterization data for these complexes matched the literature data (8, 1a). The dpm (dipivaloylmethane=2,2,6,6-tetramethylheptane-3,5-dione), glycine, and pyridine complexes were made by treating the chloride bridged dimer of PQ, BT, or BSN with the appropriate ligand.

Example 1

Synthesis of $(C^{\wedge}N)_2IrLX$ Complexes: General Procedure

The general synthesis of complexes-having acac as the $L^{\wedge}Y$ ligand will be describe. Cyclometallated Ir(III)µ-chloro-bridged dimers of a general formula $(C^{\wedge}N)_2Ir(\mu-Cl)_2(C^{\wedge}N)_2$ were synthesized according to the Nonoyama route, by refluxing $IrCl_3.(nH_2O)$ with 2-2.5 equivalents of cyclometalating ligand in a 3:1 mixture of 2-ethoxyethanol and water (Bull. Chem. Soc. Jpn. 1974, 47:767-768).

The chloro-bridged dimer complex (0.08 mmol), 0.2 mmol of acetyl acetonate and 85-90 mg of sodium carbonate are refluxed in an inert atmosphere in 2-ethoxyethanol for 12-15 hours. After cooling to room temperature, the precipitate is filtered off and washed with water, hexane, and ether. The crude product is flash chromatographed on a silica column with dichloromethane mobile phase to provide the $(C^{\wedge}N)_2IrL^{\wedge}X$ complex.

Example 2

Synthesis of iridium(III) bis(2-phenylbenzothiazolato-N, $C^2$)pyridyl chloride [BT-yl]

$[(bt)_2IrCl]_2$ (0.3 mmol) and excess pyridine were refluxed under a nitrogen atmosphere in dichloromethane (22 mL) for 90 minutes. The clear, orange-yellow solution was allowed to cool to room temperature, and the solvent was removed in vacuo. The resulting solids were washed with cyclohexane (6×15 mL), separated from the washings by filtration, and dried overnight under vacuum.

$^1$H-NMR (250 MHz, $C_6D_6$), ppm: 10.96 (d, J=8.4 Hz, 1H), 10.80 (s broad, 1H), 8.16 (s broad, 1H), 7.53 (dd, J=7.5, 1.5 Hz, 1H), 7.42 (dd, J=7.5, 1.4 Hz, 1H), 7.32 (dd, J=7.2, 1.3 Hz, 1H), 7.29 (dd, J=7.0, 1.4 Hz, 1H), 7.20-7.18 (m, 3H), 6.99-6.77 (m, 7H), 6.67 (ddd, J=7.8, 2.5, 1.4 Hz, 2H), 6.50 (dvt, J=7.5, 1.6 Hz, 1H), 6.43 (s broad, 1H), 5.90 (s broad, 1H).

Absorbance Spectrum ($C_6H_6$), nm (log ϵ): 291 (6.5), 302 (6.5), 315 (6.5), 328 (6.5), 356 (6.0), 394 (5.8), 442 (5.7), 541 (4.8).

Emission Spectrum ($C_6H_6$; room temperature) nm: 556, 596.

MS m/z: exact mass [M-Cl]$^+$: Experimental: 692.080633; Found: 692.08060; Difference −5.3 ppm.

Example 3

Synthesis of iridium(III) bis(2-(1-naphthyl)benzothiazolato-N,$C^2$)glycinate [BSN-G]

$[(bsn)_2IrCl]_2$ (0.11 mmol), glycine (0.32 mmol), and $Na_2CO_3$ (0.68 mmol) were refluxed under a nitrogen atmosphere in 2-ethoxyethanol (25 mL) for 125 minutes. The resulting red solution was allowed to cool to room temperature and diluted with methanol. This solution was then extracted with dichloromethane and water (2×). The organic layer was separated, washed with saturated NaCl solution, and dried over $Na_2SO_4$. The solvent was removed in vacuo, and the resulting solids were dried overnight on the vacuum pump. The resulting crude BSN-G was purified by column chromatography twice; first with acetonitrile, then with 9:1 acetonitrile:methanol both on silica gel.

$^1$H-NMR (500 MHz, DMSO-$d_6$) ppm: 8.54 (d, J=8.3 Hz, 2H), 8.43 (d, J=8.3 Hz, 1H), 8.37 (dd, J=16.6, 8.0 Hz, 2H), 8.16 (d, J=7.6 Hz, 1H), 7.78-7.66 (m, 4H), 7.64 (vt, J=7.4 Hz, 2H), 7.58 (vt, J=7.2 Hz, 1H), 7.50 (vt, J=7.5 Hz, 1H), 7.41 (t, J=7.6 Hz, 2H), 7.13 (t, J=9.1 Hz, 2H), 6.70 (d, J=9.1 Hz, 1H), 6.21 (d, J=8.3 Hz, 1H), 5.24 (dd broad, J=13.4, 7.3 Hz, 1H), 4.90 (dd broad, J=22.5, 9.1 Hz, 1H), 3.28-3.21 (m, 1H), 3.11 (m, 1H).

Absorbance Spectrum ($C_6H_6$), nm (log $\epsilon$): 278 (6.3), 296 (6.3), 347 (6.3), 418 (5.9), 483 (5.8), 594 (5.3).

Emission Spectrum ($C_6H_6$; room temperature) nm: 606, 656.

MS m/z: exact mass [M+Na]$^+$: Experimental: 810.08368; Found: 810.083708; Difference +6.1 ppm.

Example 4

BSN*: iridium(III) bis(2-(1-naphthyl)benzothiazolato-N,$C^2$) (2,2,6,6-tetramethyl-3,5-heptanedionato-O,O)

$^1$H-NMR (250 MHz, $CDCl_3$), ppm: 8.56 (d, J=8.2 Hz, 2H), 7.98 (ddd, J=8.2, 1.4, 0.7 Hz, 2H), 7.94 (ddd, J=7.8, 1.4, 0.7 Hz, 2H), 7.66 (d, J=8.2 Hz, 2H), 7.58 (ddd, J=8.5, 7.1, 1.4 Hz, 2H), 7.41 (ddd, J=8.5, 7.5, 1.4 Hz, 2H), 7.32 (ddd, J=7.8, 6.8, 1.0 Hz, 2H), 7.31 (ddd, J=8.5, 7.2, 1.4 Hz, 2H), 7.02 (d, J=8.2 Hz, 2H), 6.74 (d J=8.2 Hz, 2H), 5.32 (s, 1H), 0.75 (s, 9H).

Absorbance Spectrum ($C_6H_6$), nm (log $\epsilon$): 278 (6.7), 304 (6.6), 335 (6.5), 341 (6.5), 430 (6.0), 481 (6.1), 517 (6.0), 602 (5.0).

Emission Spectrum ($C_6H_6$; room temperature) nm: 610, 662.

MS m/z: 896 [M]$^+$ (not observed), 713 [M-dpm]$^+$, 401 [M-dpm-bsn]$^+$, 355 [M-dpm-bsn-$C_4H_4$]$^+$, 260 [M-dpm-bsn-Ir]$^+$, 185 [M-bsn-bsn-Ir]$^+$.

Elemental Analysis: ($C_{45}H_{39}IrN_2O_2S_2$) Experimental: C: 60.31%, H: 4.39%, N, 3.13%. Found: C: 59.88%, H: 4.14%, N: 3.20%.

Example 5

Stern-Volmer Experimental

Solutions of BSN*, PQ, and BT were prepared in toluene to have an optical density of approximately 0.1 at 365 nm. These solutions were placed in sealed quartz cuvettes and exposed to atmospheres of varying ratios of oxygen and nitrogen ($O_2/N_2$: 25/75, 50/50, 75/25, 100/0) by bubbling a flow of gas at 29 mL/min for 5 minutes. A fifth sample of each solution was rigorously degassed via a freeze/pump method. The solution was frozen in a slush of dry ice and acetone for 20 minutes, exposed to vacuum for 20 minutes, and then allowed to return to room temperature.

Assuming that bubbling at a rate of 29 mL/min for 5 minutes saturates the solution with gas (bubbling for longer than 5 minutes gave the same results as bubbling for 5 minutes), the concentration of oxygen that is dissolved in the solutions can be calculated using Henry's Law (C=H×P; C: concentration of dissolved gas (mol/L); H: Henry's Law Constant for that gas; P: partial pressure of that gas in the gas mixture (atm)). Fogg and Gerrard reported that the mole fraction solubility of oxygen in toluene at equilibrium with one atmosphere of pure oxygen is 0.000923 (9). Dividing the mole fraction of oxygen by the volume of one mole of toluene (0.1065 L), an oxygen concentration of 0.00867 M for oxygen-saturated toluene was calculated. Knowing this, the Henry's Law Constant for oxygen in toluene can be calculated as 0.00867 Ml atm.

Digital flow meters were used to obtain the mixtures of oxygen and nitrogen. Using the densities and molecular masses of oxygen and nitrogen, the flow rates of mL/min were converted to mol/min, and dividing the molar flow rates by the total molar flow rate produces the mole fraction of the gas mixture. Then, assuming that the solution is saturated with the gas mixture, the mole fraction of oxygen in the solution is the same as that in the gas above the solution. Because the solutions were kept under a total pressure of one atmosphere, the partial pressure of oxygen is equal to the mole fraction of oxygen. Thus, multiplying the mole fraction of oxygen in the gas mixture by 0.00867 yields the concentration of oxygen in the solution.

Figure 3:
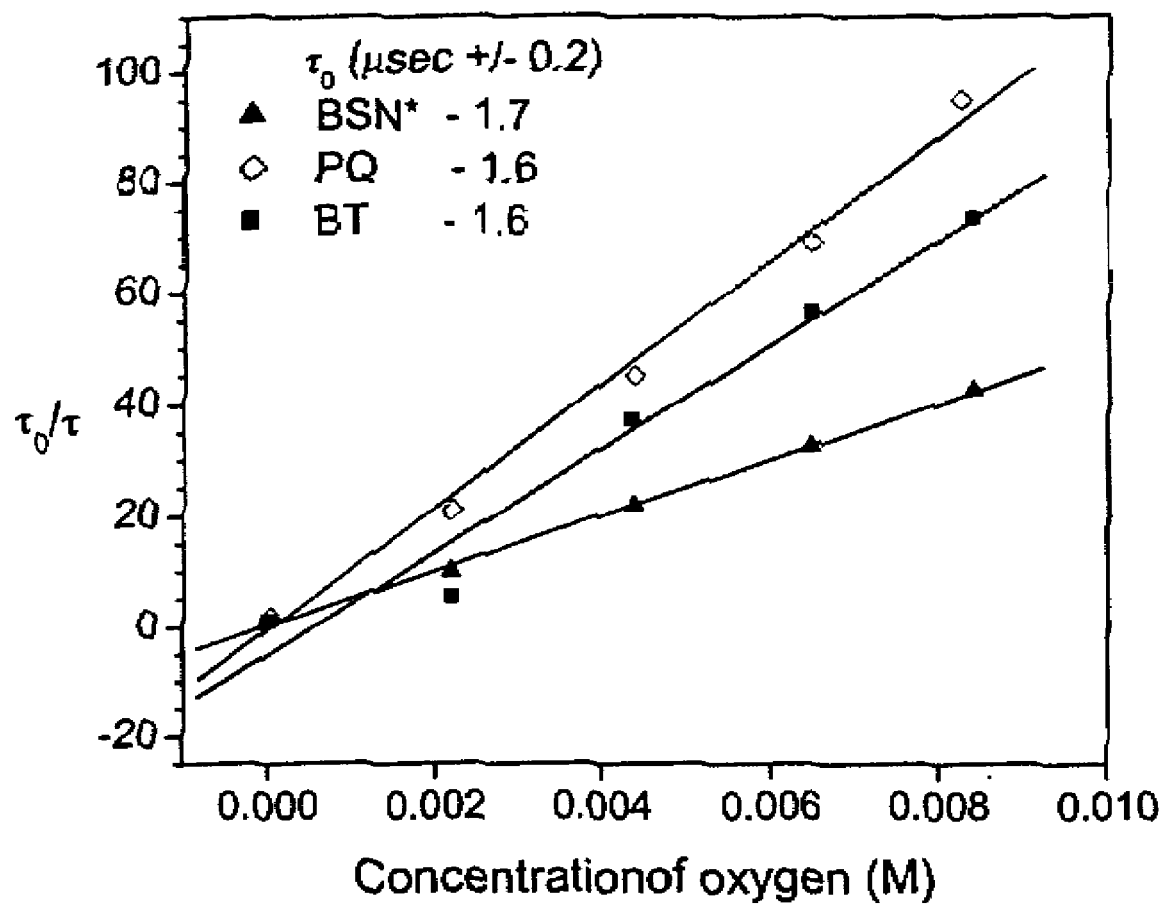
FIG. 3 is a graph of singlet oxygen intensity vs. the molar concentration of oxygen.

A Nd:YAG laser operating at its second harmonic (532 nm) was used to pump a dye laser (LDS750 in methanol) to generate a beam of 730 nm photons. This beam was doubled in a KDP crystal to generate 365 nm photons at 10 Hz with a FWHM of approximately 9 ns. This 365 nm beam was used to measure the phosphorescent lifetimes of these samples. The emission of the samples was collected at a right angle to the pump beam through a 399 nm cut-off filter (470 nm for BT-G) into a Thorlabs Model DET210 photodiode that is sensitive to 200-1100 nm light. Each sample was measured three times vs. a toluene blank at 200 shots/point for 15,000 data points ranging approximately from −1 to 20 µs relative to the pump pulse. The six data files (three sample and three blank) were summed to give a single, overall data file, which was then fit to an exponential ($y=y_0+Ae^{-x^\tau}$) using Origin 6.1 to extract the lifetime ($\tau$). Plotting $\tau_0/\tau$ vs. the molar concentration of oxygen yields a straight line, the slope of which contains the quenching rate constant, $k_{qSV}$ (slope=$k_{qSV} \times \tau_0$) (FIG. 3 and Table 2).

TABLE 2

| | [$O_2$] (M) | $\tau$ (sec) | $\tau_0/\tau$ | slope | $k_{qSV}$ ($M^{-1}s^{-1}$) |
|---|---|---|---|---|---|
| BSN* | 0 | 1.72E−06 | 1 | | 2.90E+09 |
| | 0.002159 | 1.75E−07 | 9.85 | | |
| | 0.004347 | 7.90E−08 | 21.78 | 4998 | |
| | 0.006454 | 5.33E−08 | 32.3 | | |
| | 0.008378 | 4.06E−08 | 42.41 | | |
| PQ | 0 | 1.58E−06 | 1 | | 7.20E+09 |
| | 0.002159 | 7.60E−08 | 20.83 | | |
| | 0.004347 | 3.52E−08 | 45 | 11333 | |
| | 0.006454 | 2.29E−08 | 68.98 | | |
| | 0.008242 | 1.67E−08 | 94.99 | | |
| BT | 0 | 1.58E−06 | 1 | | 5.90E+09 |
| | 0.002159 | 2.99E−07 | 5.3 | | |
| | 0.004347 | 4.25E−08 | 37.29 | 9324 | |
| | 0.006454 | 2.81E−08 | 56.45 | | |
| | 0.008378 | 2.15E−08 | 73.59 | | |

Example 6

Quantum Yield Measurements

Figure 4:
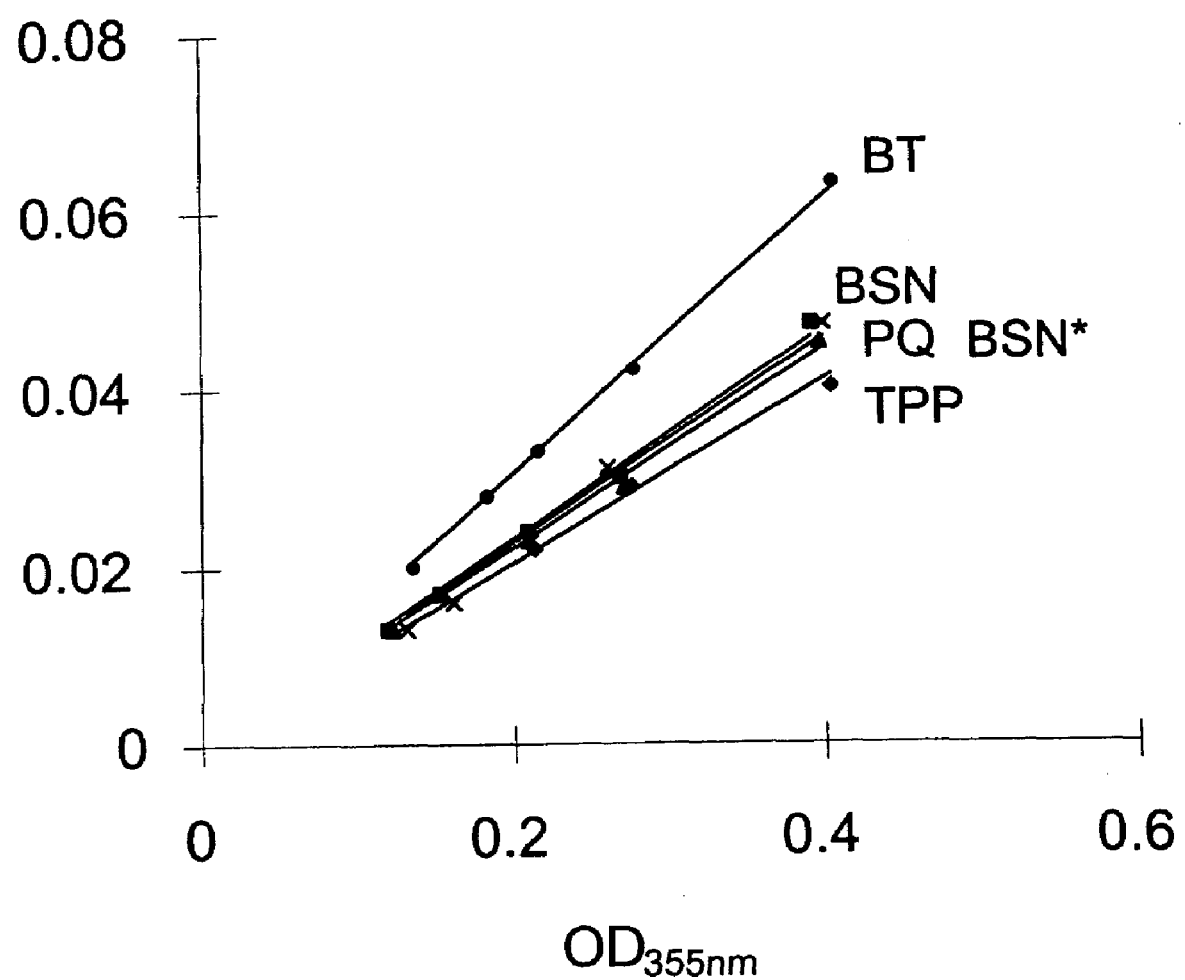
FIG. 4 is a graph of the relative intensity of singlet oxygen production vs. absorbance for the Ir(III) complexes BSN, BSN*, PQ, and BT and for the reference TPP at 355 nm excitation.
Figure 5:
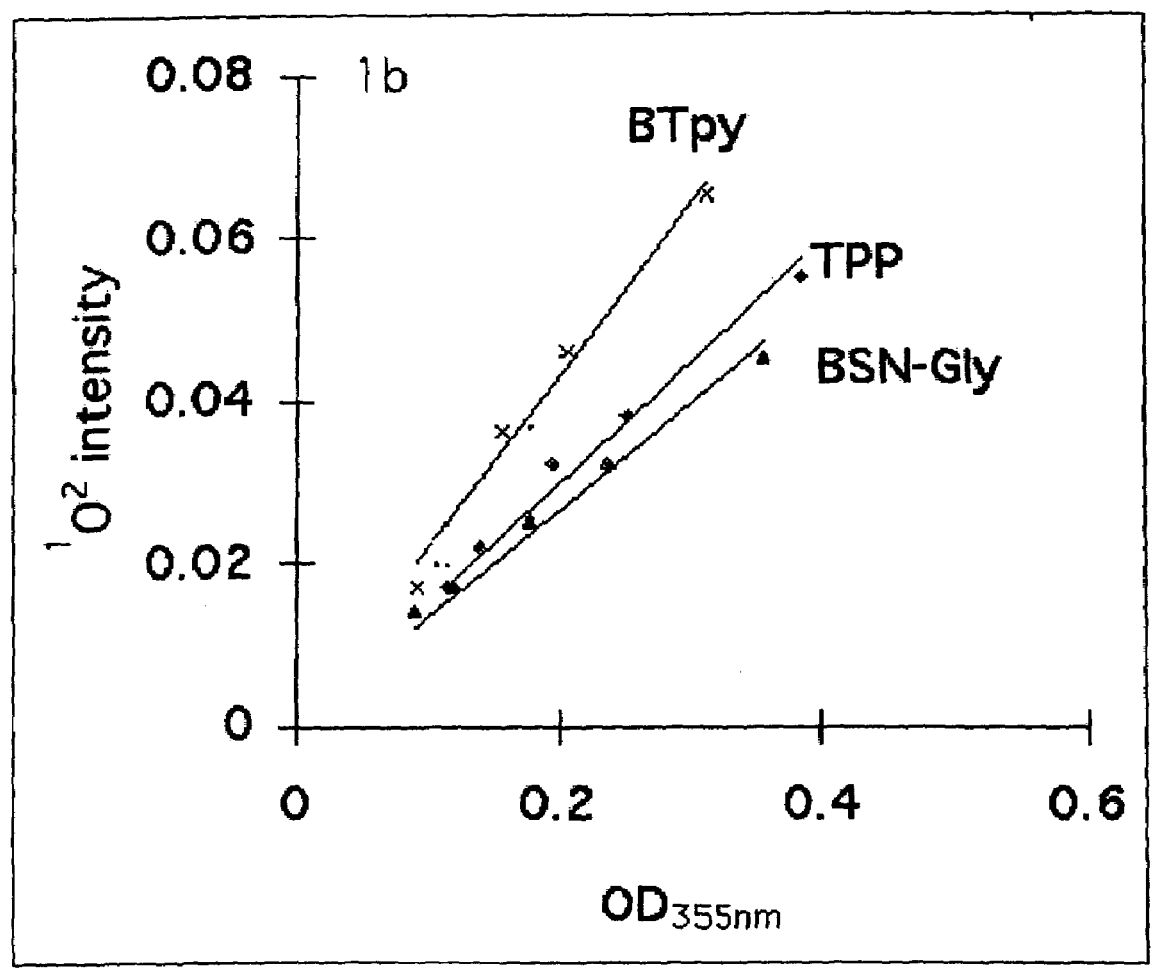
FIG. 5 is a graph of the relative intensity of singlet oxygen production vs. absorbance for the Ir(III) complexes BSN-Gly and BT-py and for at 355 nm excitation.
Figure 6:
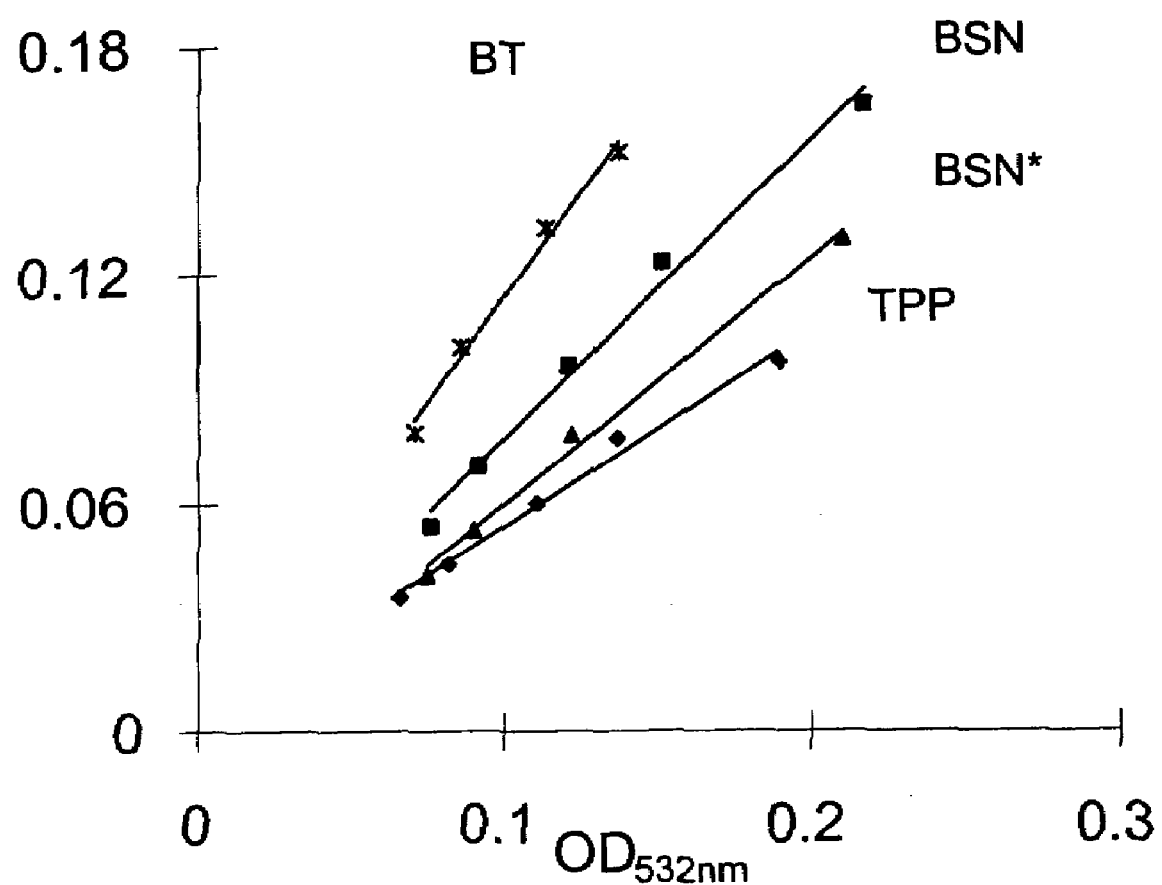
FIG. 6 is a graph of the relative intensity of singlet oxygen production vs. absorbance for the Ir(III) complexes BSN, BSN*, and BT and for the reference TPP at 532 nm excitation.

Samples for the quantum yield measurements for singlet oxygen production for the complexes studied are given in FIGS. 4, 5, and 6. The quantum yields were obtained by measuring the intensity of the $^1O_2$ luminescence signal ($\lambda_{max}$=1268 nm), with a liquid nitrogen cooled germanium photodiode. Measurements were taken at 355 and 532 nm excitation, in air-saturated solutions, with TPP, C60 and Perinaphthenone as references. The optical density of the photosensitizer solutions was generally kept between 0.05 and 0.4 at 355 nm excitation wavelength, and 0.03 and 0.2 at 532 nm excitation wavelength.

Figure 7:
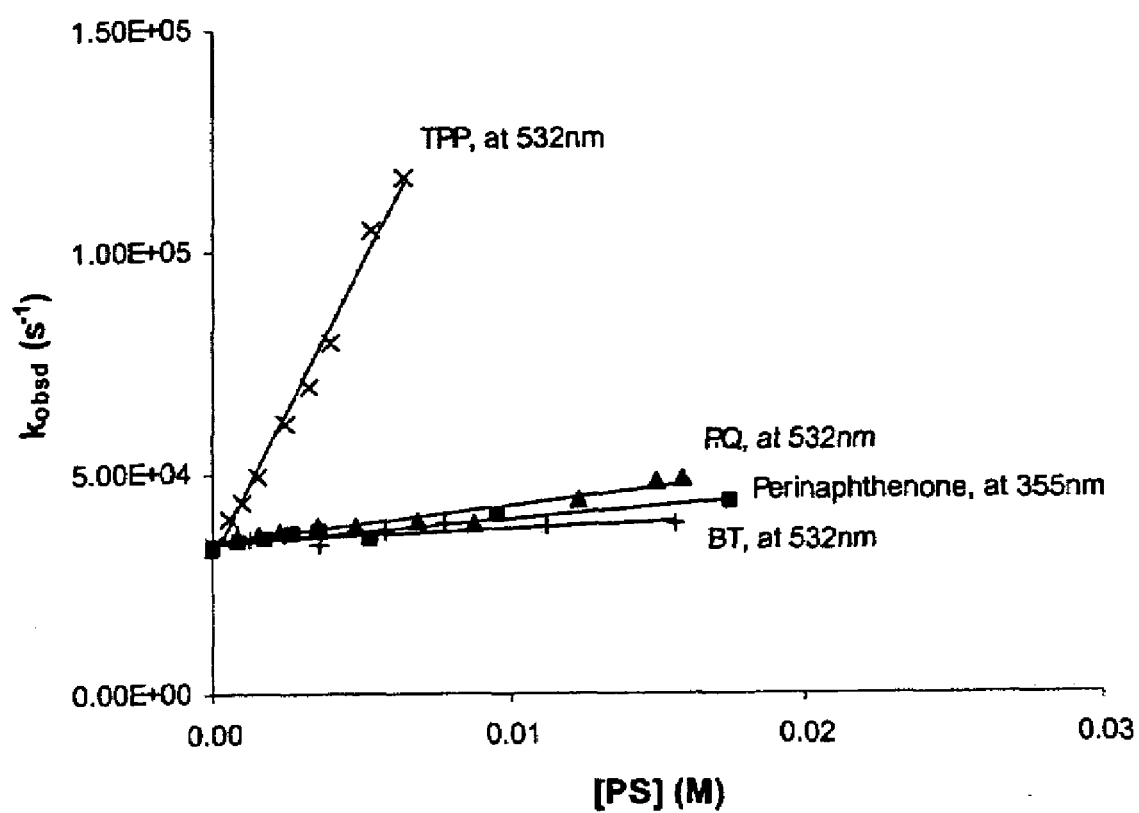
FIG. 7 is a graph showing the effects of [PS] on the initial intensities of $^1O_2$ in benzene the Ir(III) complexes PQ and PT, and for the reference TPP.
Figure 8:
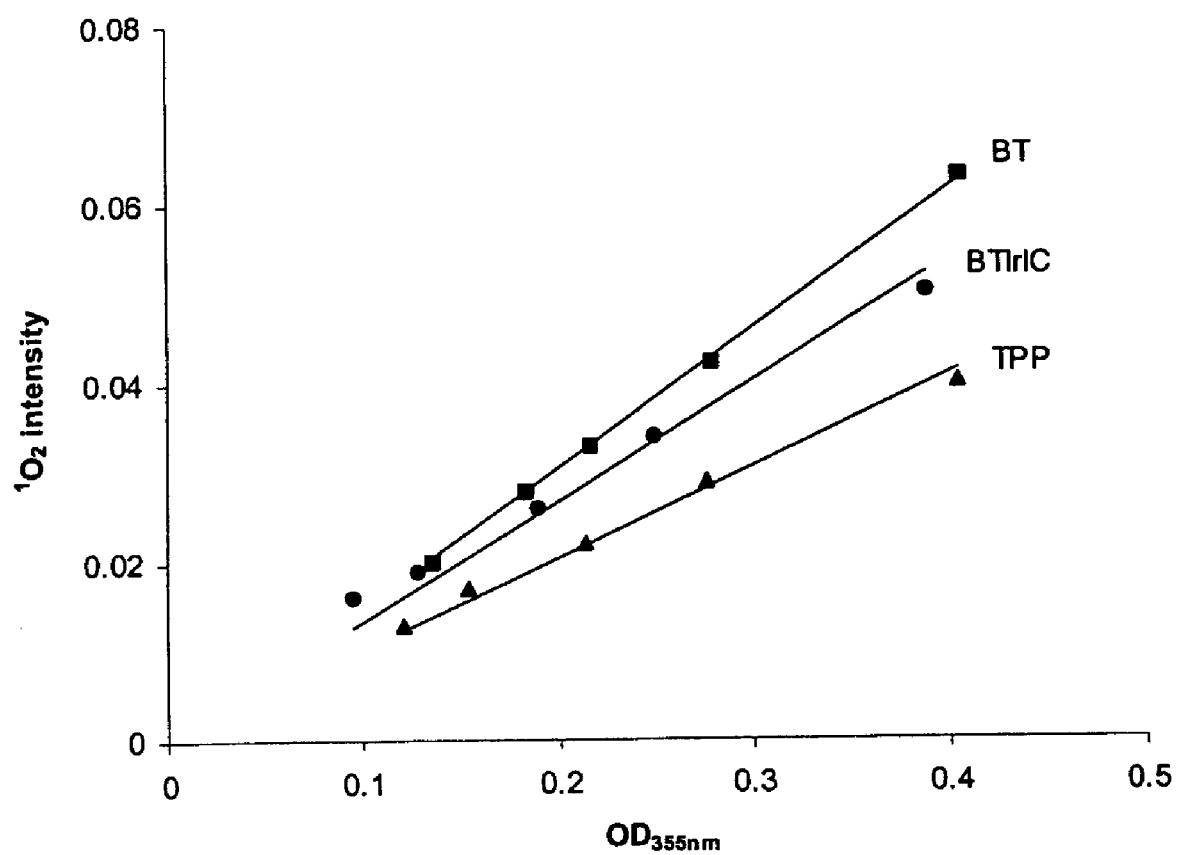
FIG. 8 is a graph of the relative intensity of singlet oxygen production vs. absorbance for the Ir(III) complexes BT and BTI$_r$IC, and for the reference TPP.

6-10 times. Singlet oxygen quenching rate constants by the Ir(III) complexes were obtained from the slopes of Stern Volmer plots (See FIG. 7).

Table 3 provides quantum yields and singlet oxygen quenching rates for Ir(III) and Pt(II) complexes of this invention. $E_{em}$(eV)=the emission maximum energy in eV at room temperature, as determined from the phosphorescence spectrum; $\Phi_{PE}$=the quantum efficiency for emission in solution; $\tau_{PE}$=the emission lifetime at room temperature or 77K (in solution). The structures of the complexes are shown in FIGS. 1A-1E.

TABLE 3

| No. | Photosensitizer | $\Phi_{\Delta 355\,nm}$ | $\Phi_{\Delta 532\,nm}$d | $k_q$ (M$^{-1}$s$^{-1}$) | $\lambda_{em}$ (nm)[e] | $E_{em}$ (eV) | $\Phi_{PE}$[e] | E(Sen$^{+/0}$) (V)[f] | E(Sen$^{+/*}$) (V)[g] |
|---|---|---|---|---|---|---|---|---|---|
| 1 | btpPt(acac) | 1.02 ± 0.10 | | (6.9 ± 1.2) × 10$^6$ | 600 | 2.07 | 0.08 | | |
| 2 | btpPt(dpm) | 1.04 ± 0.05 | | (7.0 ± 1.1) × 10$^6$ | 600 | 2.07 | | | |
| 3 | ppyPt(acac) | 0.98 ± 0.12 | | (1.5 ± 0.4) × 10$^7$ | 480 | 2.58 | 0.15 | 0.60 | -1.29 |
| 4 | ppyPt(dpm) | 0.95 ± 0.09 | | (2.2 ± 0.6) × 10$^7$ | 477 | 2.60 | | | |
| 5 | btPt(dpm) | 1.03 ± 0.10 | | (7.7 ± 1.5) × 10$^6$ | 530 | 2.34 | | | |
| 6 | C$_6$Pt(acac) | 0.81 ± 0.05 | | No sample | 590 | 2.10 | 0.25 | | |
| 7 | (bpy)PtMe$_2$ | 0 | 0 | (2.4 ± 0.1) × 10$^9$ | | | | | |
| 8 | (Phen)PtMe$_2$ | 0 | 0 | (2.0 ± 0.2) × 10$^9$ | | | | | |
| 9 | (CyPh$_2$)PtMe$_2$ | 0 | 0 | (1.5 ± 0.1) × 10$^9$ | | | | | |
| 10 | (PhenPh$_2$)PtMe$_2$ | 0 | 0 | (1.7 ± 0.2) × 10$^9$ | | | | | |
| 11 | (tbbpy)PtMe$_2$ | 0 | 0 | (1.6 ± 0.3) × 10$^9$ | | | | | |
| 12 | (bt)$_2$Ir(acac)[a] | 0.86 ± 0.07 | 1.00 ± 0.07 | (5.0 ± 2.0) × 10$^5$ | 557 | 2.23 | 0.26 | 0.56 | -0.98 |
| 13 | (bt)$_2$Ir(py)[a] | 0.95 ± 0.09 | 1.00 ± 0.09 | Not soluble | 558 | 2.23 | 0.2 | | |
| 14 | (C$_6$)$_2$Ir(acac) | 0.60 ± 0.04 | | (5.5 ± 1.2) × 10$^6$ | 585 | 2.11 | 0.6 | 0.58 | -0.84 |
| 15 | (bo)$_2$Ir(acac) | 0.76 ± 0.06 | | (1.8 ± 0.3) × 10$^5$ | 525 | 2.36 | 0.25 | | |
| 16 | (pq)$_2$Ir(acac)[a] | 0.62 ± 0.05 | 0.98 ± 0.07 | (1.0 ± 0.2) × 10$^6$ | 597 | 2.08 | 0.1 | 0.43 | -0.96 |
| 17 | (1Np)$_2$Ir(acac) | 0.76 ± 0.05 | | Not soluble | 595 | 2.09 | 0.2 | | |
| 18 | (bsn)$_2$Ir(acac)[a] | 0.59 ± 0.07 | 0.89 ± 0.02 | (6.3 ± 0.2) × 10$^6$ | 606 | 2.05 | 0.22 | 0.55 | -0.81 |
| 19 | (bsn)$_2$Ir(dpm)[a] | 0.60 ± 0.06 | 0.77 ± 0.08 | (4.0 ± 0.3) × 10$^6$ | 594 | 2.09 | 0.16 | | |
| | (bsn)$_2$Ir(dpm)[c] | 0.69 ± 0.05 | | Not soluble | 594 | 2.09 | | | |
| 20 | bsn-g[a] | 0.54 ± 0.02 | 0.81 ± 0.06 | (2.1 ± 0.5) × 10$^6$ | 606 | 2.05 | | | |
| | bsn-g[c] | 0.62 ± 0.05 | | Not soluble | 606 | 2.05 | | | |
| 21 | (ppy)$_2$Ir(acac) | 0.90 ± 0.05 | | No sample | 516 | 2.40 | 0.34 | 0.46 | -1.16 |
| 22 | (ppy)$_3$Ir[b] | 0.92 ± 0.07 | | Not soluble | | | | 0.32 | -1.45 |
| 23 | (btp)$_2$Ir(acac) | 0.72 ± 0.06 | | Not soluble | 612 | 2.03 | 0.21 | 0.36 | -0.98 |
| | (btp)$_2$Ir(acac)[c] | 0.69 ± 0.04 | | Not soluble | | | | | |
| 24 | Firpic | 1.08 ± 0.12 | | Not soluble | 467 | 2.66 | 0.6 | 0.89 | -1.08 |
| | Firpic[c] | 0.84 ± 0.05 | | Not soluble | | | | | |
| 25 | Pqaet[c] | 0.69 ± 0.01 | | (3.9 ± 1.7) × 10$^5$ | 587 | 2.12 | | | |
| 26 | MPIp[3] | 0.27 ± 0.02 | | (2.5 ± 0.4) × 10$^7$ | 673 | 1.85 | | | |
| | MPIp[3c] | 0.57 ± 0.05 | | (2.6 ± 0.2) × 10$^7$ | 673 | 1.85 | | | |
| 27 | 1Np p[3c] | 0.71 ± 0.01 | | Not soluble | 615 | 2.02 | | | |
| 28 | Bt p[2c] | 0.78 ± 0.04 | | (2.9 ± 1.1) × 10$^6$ | 557 | 2.23 | 0.1 | | |

[a]Structural formula are in: J. Am. Chem. Soc. 2002, 124, 14828-14829.
[b]Tris-(2-phenyl pyridinato, N, C$^{2'}$) iridium (III)
[c]Measured in MeOD
[d]Only measured if compounds absorb at 532 nm.
[e]Results for Iridium and platinum complexes are from references J. Am. Chem. Soc. 2001, 123, 4304-4312 and Inorg. Chem. 2002, 41, 3055-3066.
[f]Oxidation potentials vs. ferrocene/ferrocenium (CP$_2$Fe/Cp$_2$Fe$^+$)
[g]Excited state redox potentials vs. NHE, E(Sen$^{+/*}$) = D(Sen$^{+/0}$) − E$_{00}$. E$_{00}$ is estimated using E$_{em}$ (eV.)

Example 7

Determination of Singlet Oxygen Luminescence Quenching Rate Constants

TPP in benzene or chloroform with OD 0.5-0.7 was used as blank/solvent solution to produce singlet oxygen. The intensity of $^1O_2$ luminescence signals was measured at 532 nm excitation in air-saturated solutions with a liquid nitrogen cooled germanium photodiode at 1268 nm. 0.02-0.5 mL quencher stock solution of Ir(III) complexes in 0.5-2 M was added to the blank solution. The decay trace of singlet oxygen was then re-measured, and the additions repeated The foregoing description is considered as illustrative only of the principles of the invention. Further, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

REFERENCES 1. (a) S. Lamansky, P. Djurovich, D. Murphy, F. Abdel-Razzaq, H.-E. Lee, C. Adachi, P. E. Burrows, S. R. Forrest, M. E. Thompson, *J. Am. Chem. Soc.*, 2001, 123, 4304-4312. (b) S. Lamansky, R. C. Kwong, M. Nugent, P. I. Djurovich, M. E. Thompson, *Org. Elect.*, 2001, 2, 53-62. (c) Ikai, M.; Tokito, S.; Sakamoto, Y.; Suzuki, T.; Taga, Y. *Appl. Phys. Lett.*, 2001, 79, 156-158. (d) Adachi, C.; Baldo, M. A.; Forrest, S. R.; Thompson, M. E. *J. Appl. Phys.*, 2001, 90, 4058.
2. (a) Lo, K. K.-W.; Ng, D. C.-M.; Chung, C.-K. *Organometallics*, 2001, 20, 4999-5001. (b) Di Marco, G.; Lanza, M.; Mamo, A.; Stefio, I.; Di Pietro, C.; Romeo, G.; Campagna, S. *Anal. Chem.*, 1998 70, 5019-5023. (c) Amao, Y.; Ishikawa, Y.; Okura, I. *Anal. Chim. Acta*, 2001, 445, 177-182.
3. S. Lamansky, P. Djurovich, D. Murphy, F. Abdel-Razaq, R. Kwong, I. Tsyba, M. Bortz, B. Mui, R. Bau, M. E. Thompson, *Inorg. Chem.*, 2001, 40(7), 1704-1711.
4. Demas, J. N.; Harris, E. W.; McBride, R. P. *J. Am. Chem. Soc.*, 1977, 99, 3547-3551. Demas, J. N.; Harris, E. W.; Flynn, C. M.; Diemente, D. *J. Am. Chem. Soc.*, 1975, 97, 3838-3839.
5. Selke, M.; Foote, C. S.; Karney, W. L. *Inorg. Chem.*, 1995, 34, 5715-5720.
6. Ogilby, P. R.; Foote, C. S. *J. Am. Chem. Soc.*, 1983, 105, 3423-3430.
7. (a) Cadet, J.; Vigny, P. In *The Photochemistry of Nucleic Acids*; Morrison, H., Ed.; John Wiley and Sons: New York,; 1990; pp 1-272; (b) Foote, C. S.; Clennan, E. L. In *Active Oxygen in Chemistry*; Foote, C. S.; Valentine, J. S. Greenberg, A.; Liebman, J. F., Eds.; Blackie Academic and Professional (Chapman & Hall): New York, 1995; Chapter 4.
8. Urban, R; Kramer R,; Mihan S,; Polborn K.; Wagner B.; Beck W *J. Organomet. Chem.*, 1998, 517, 191-200.
9. Fogg, P. G. T. and Gerrard, W., "Solubility of Gases in Liquids." Wiley, New York, 1991.
10. Y. Cao, I. D. Parker, G. Yu, C. Zhang, A. J. Heeger, *Nature*, 1999, 397, 414.
11. V. Cleave, G. Yahioglu, P. Le Barny, R. H. Friend, N. Tessler, *Adv. Mater.*, 1999, 22, 396.
12. C. Adachi, M. Baldo, S. R. Forrest, M. E. Thompson, *Appl. Phys. Lett.*, 2000, 77, 904.
13. J. S. Huang, H. F. Zhang, W J. Tian, J. Y. Hou, Y. G. Ma, J. C. Shen, S. Y. Liu, *Synth. Met.*, 1997, 87, 105.
14. M. J. Yang, T. Tsutsui, *Jpn. Appl. Phys.*, 2000, 39, L828.

What is claimed is:

1. An organometallic singlet oxygen photosensitizer, comprising a metal and one or more ligands, wherein at least one of said ligands has a carbon atom that is covalently bonded to the metal, comprising the formula $(C\textasciicircum X)_n MY_m L_p$
    where M is a metal;
    n+m is 3 when M is trivalent or n+m is 2 when M is divalent;
    Y is a monoanionic ligand;
    L is a neutral ligand;
    or optionally when M is Ir(III) then Y and L are absent;
    $C\textasciicircum X$ is a bidentate cyclometallated ligand wherein each $C\textasciicircum X$ is the same or different;
    and X is N, O, S, P or C,
    wherein at least one of said $C\textasciicircum X$, Y or L ligands is further coupled to a moiety that can bind to a biomolecule, a cell or biological tissue.

2. The organometallic singlet oxygen photosensitizer of claim 1, wherein at least one of said ligands is a bidentate cyclometallated organometallic ligand.
3. The organometallic singlet oxygen photosensitizer of claim 1, wherein said metal has an atomic number of at least 40.
4. The organometallic singlet oxygen photosensitizer of claim 1, wherein said metal is selected from the group consisting of Zr, Hf, V, Nb, Ta, Cr, Mo, W, Mn, Tc, Re, Fe, Ru, Os, Co, Rh, Ir, Ni, Pd, Pt, Tl, Pb, Bi, In, Sn, Sb, Te, Au, and Ag.
5. The organometallic singlet oxygen photosensitizer of claim 1, wherein M is Ir(III) or Pt(II).
6. The photosensitizer of claim 1, wherein Y is Cl.
7. The photosensitizer of claim 1, wherein L is

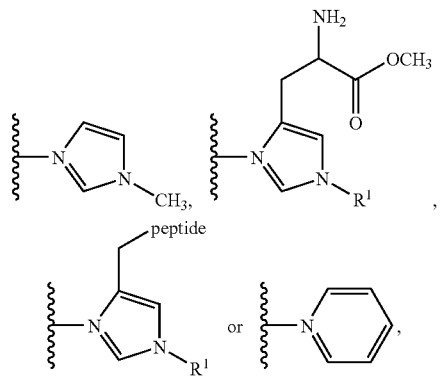

and
$R^1$ is H or alkyl.

8. The photosensitizer of claim 1, wherein $C\textasciicircum X$ is

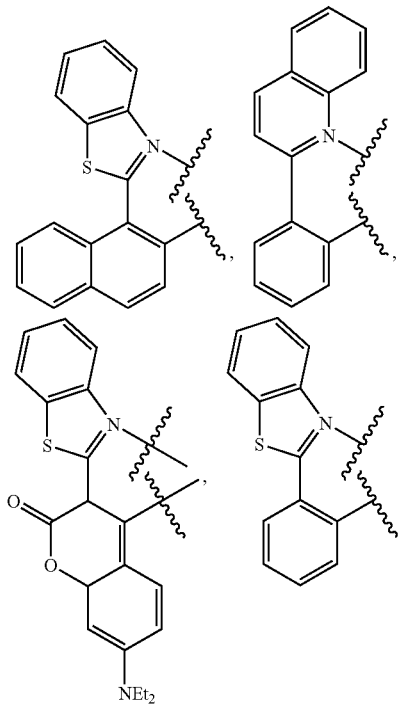

-continued

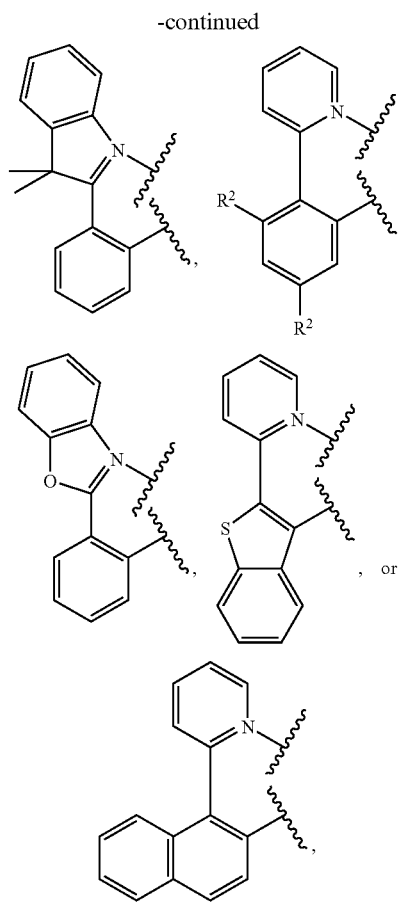

and R² is H or F.

9. An organometallic singlet oxygen photosensitizer, comprising a metal and one or more ligands, wherein at least one of said ligands has a carbon atom that is covalently bonded to the metal, having the formula $C^\wedge X_n M(L^\wedge Y)_m$ wherein M is a metal;

n+m is 2 when M is divalent or n+m is 3 when M is trivalent;

C^X is a first bidentate cyclometallated ligand wherein each C^X is the same or different;

L^Y is a second bidentate cyclometallated ligand wherein each L^Y is the same or different; and X, Y and L are independently N, O, S, P or C, wherein at least one of said C^X or L^Y ligands is further coupled to a moiety that can bind to a biomolecule or biological tissue.

10. The organometallic singlet oxygen photosensitizer of claim 9, wherein said metal is selected from the group consisting of Zr, Hf, V, Nb, Ta, Cr, Mo, W, Mn, Tc, Re, Fe, Ru, Os, Co, Rh, Ir, Ni, Pd, Pt, Tl, Pb, Bi, In, Sn, Sb, Te, Au, and Ag.

11. The organometallic singlet oxygen photosensitizer of claim 9, wherein M is Ir(III) or Pt(II).

12. The singlet oxygen photosensitizer of claim 9, wherein C^X is

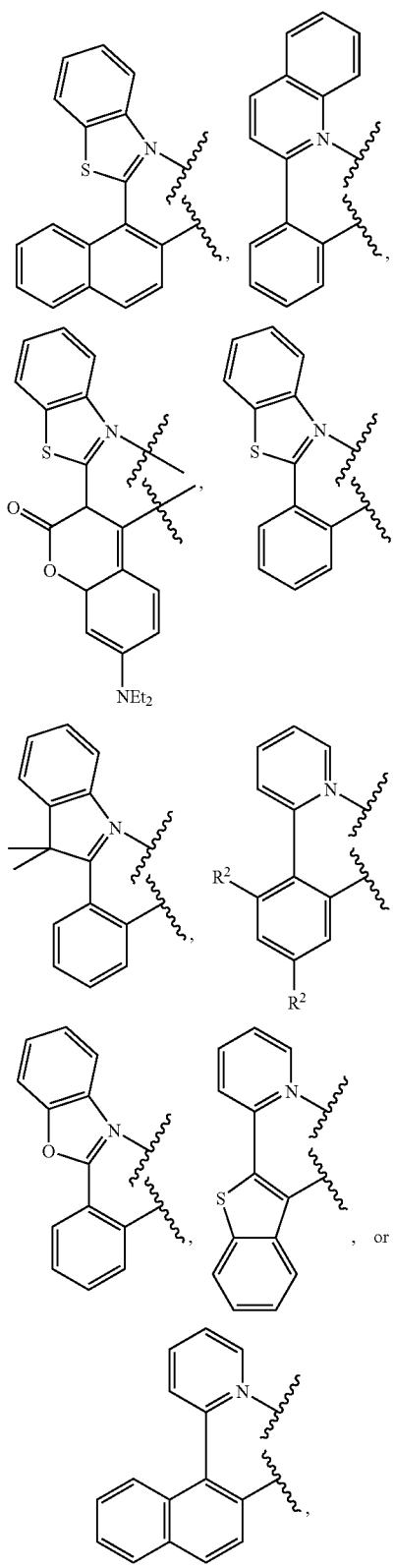

and R² is H or F.

13. The singlet oxygen photosensitizer of claim 9, wherein L^Y is

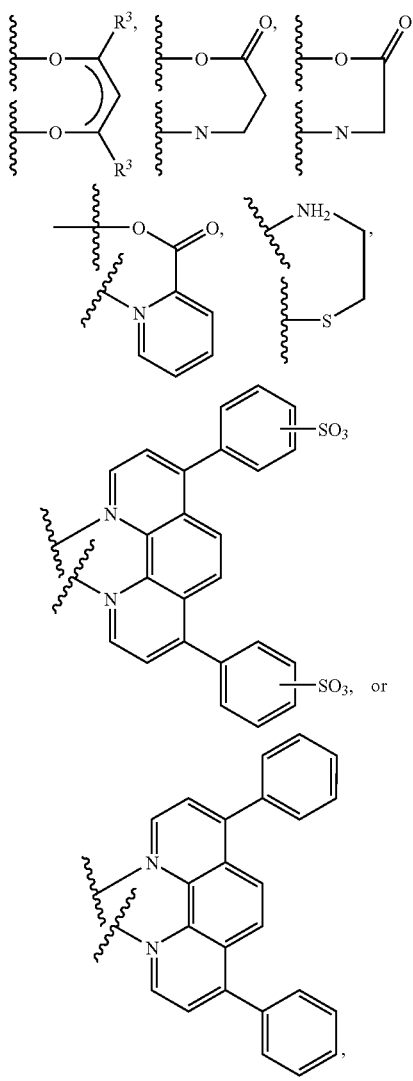

and R³ is CH₃ or t-butyl.

14. An organometallic singlet oxygen photosensitizer, comprising a metal and one or more ligands, wherein at least one of said ligands has a carbon atom that is covalently bonded to the metal, having the formula $(C\wedge X)_n M(C\wedge X')_m$ wherein M is a metal;

n+m is 3 when M is trivalent and n+m is 2 when M is divalent;

C^X and C^X' are first and second bidentate cyclometallated ligands, respectively, wherein each C^X and C^X' is the same or different; and X and X' are independently N, O, S, P or C, wherein at least one of said C^X or C^X' ligands is further coupled to a moiety that can bind to a biomolecule or biological tissue.

15. The organometallic singlet oxygen photosensitizer of claim 14, wherein said metal is selected from the group consisting of Zr, Hf, V, Nb, Ta, Cr, Mo, W, Mn, Tc, Re, Fe, Ru, Os, Co, Rh, Ir, Ni, Pd, Pt, Tl, Pb, Bi, In, Sn, Sb, Te, Au, and Ag.

16. The organometallic singlet oxygen photosensitizer of claim 14, wherein M is Ir(III) or Pt(II).

17. The organometallic singlet oxygen photosensitizer of claim 14, wherein C^X and C^X' are independently

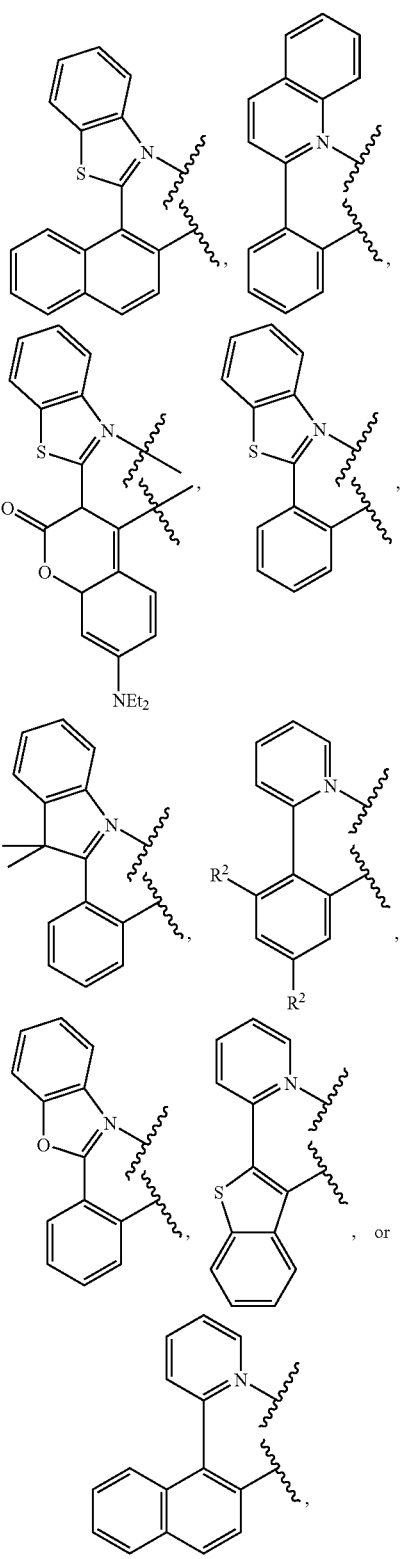

and R² is H or F.

18. An organometallic singlet oxygen photosensitizer, comprising a metal and one or more ligands, wherein at least one of said ligands has a carbon atom that is covalently bonded to the metal, having the formula (C^X)$_3$Ir, where C^X is a cyclometallated ligand, wherein each C^X is the same or different; and X is N, O, S, P or C, wherein said C^X ligand is further coupled to a moiety that can bind to a biomolecule or biological tissue.

19. The singlet oxygen sensitizer of claim 18, comprising the formula

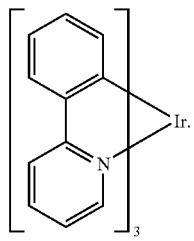

20. A method of studying oxidative damage to a biological material via photogenerated singlet oxygen, comprising:
reacting the biological material with an Iridium dimer under conditions that allow the dimer to be cleaved by said biological material, said Iridium dimer comprising the formula:

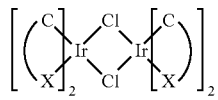

wherein X is N, O, S, P or C,
whereby a complex between said cleaved Iridium dimer and said biological material is formed;
irradiating said complex; and
measuring the quantum yield for singlet oxygen production, wherein the amount of singlet oxygen produced is proportional of the amount of oxidative damage.

21. The method of claim 20, wherein the biological material comprises a peptide or protein.

22. A method of light-induced singlet oxygen production comprising subjection of a photosensitizer of claim 1 to light in the presence of oxygen.

23. A method of light-induced singlet oxygen production comprising subjection of a photosensitizer of claim 9 to light in the presence of oxygen.

24. A method of light-induced singlet oxygen production comprising subjection of a photosensitizer of claim 14 to light in the presence of oxygen.

25. A method of light-induced singlet oxygen production comprising subjection of a photosensitizer of claim 18 to light in the presence of oxygen.

26. A method for causing photodynamic damage to target cells or biological tissue, said method comprising:
contacting the target cells or tissue with a photosensitizer of claim 1 so as to produce a population of treated cells or biological tissue; and
exposing the population of treated cells to light at a wavelength that activates the photosensitizer, thereby producing singlet oxygen and causing photodynamic damage to the target cells or biological tissue.

27. A method for causing photodynamic damage to target cells or biological tissue, said method comprising:
contacting the target cells with a photosensitizer of claim 9 so as to produce a population of treated cells or biological tissue; and
exposing the population of treated cells to light at a wavelength that activates the photosensitizer, thereby producing singlet oxygen and causing photodynamic damage to the target cells or biological tissue.

28. A method for causing photodynamic damage to target cells or biological tissue, said method comprising:
contacting the target cells with a photosensitizer of claim 14 so as to produce a population of treated cells or biological tissue; and
exposing the population of treated cells to light at a wavelength that activates the photosensitizer, thereby producing singlet oxygen and causing photodynamic damage to the target cells or biological tissue.

29. A method for causing photodynamic damage to target cells or biological tissue, said method comprising:
contacting the target cells with a photosensitizer of claim 18 so as to produce a population of treated cells or biological tissue; and
exposing the population of treated cells to light at a wavelength that activates the photosensitizer, thereby producing singlet oxygen and causing photodynamic damage to the target cells or biological tissue.

30. A process for treating aqueous waste effluents containing organic materials which comprises adding to said aqueous effluents in the presence of oxygen a photosensitizer of claim 1, and then photolyzing the resulting suspension with visible light or with light having wavelengths between 400 nm and about 800 nm.

31. The process of claim 30, wherein the sensitizer is covalently attached to a polymer support.

32. A process for treating aqueous waste effluents containing organic materials which comprises adding to said aqueous effluents in the presence of oxygen a photosensitizer of claim 9, and then photolyzing the resulting suspension with visible light or with light having wavelengths between 400 nm and about 800 nm.

33. The process of claim 32, wherein the sensitizer is covalently attached to a polymer support.

34. A process for treating aqueous waste effluents containing organic materials which comprises adding to said aqueous effluents in the presence of oxygen a photosensitizer of claim 14, and then photolyzing the resulting suspension with visible light or with light having wavelengths between 400 nm and about 800 nm.

35. The process of claim 34, wherein the sensitizer is covalently attached to a polymer support.

36. A process for treating aqueous waste effluents containing organic materials which comprises adding to said aqueous effluents in the presence of oxygen a photosensitizer of claim 18, and then photolyzing the resulting suspension with visible light or with light having wavelengths between 400 nm and about 800 nm.

37. The process of claim 36, wherein the sensitizer is covalently attached to a polymer support.

* * * * *